(12) United States Patent
Padget et al.

(10) Patent No.: US 7,326,211 B2
(45) Date of Patent: Feb. 5, 2008

(54) DEPLOYMENT TOOL FOR DISTAL BONE ANCHORS WITH SECONDARY COMPRESSION

(75) Inventors: Martin Padget, Valencia, CA (US); Brad S. Culbert, Rancho Santa Margarita, CA (US)

(73) Assignee: Interventional Spine, Inc., Irvine, CA (US)

( * ) Notice: Subject to any disclaimer, the term of this patent is extended or adjusted under 35 U.S.C. 154(b) by 134 days.

(21) Appl. No.: 10/790,671

(22) Filed: Mar. 1, 2004

(65) Prior Publication Data

US 2004/0260289 A1    Dec. 23, 2004

Related U.S. Application Data

(63) Continuation-in-part of application No. 09/991,367, filed on Nov. 13, 2001, now Pat. No. 6,890,333, which is a continuation-in-part of application No. 09/934,467, filed on Aug. 23, 2001, now Pat. No. 6,551,481.

(60) Provisional application No. 60/464,398, filed on Apr. 21, 2003, provisional application No. 60/451,296, filed on Feb. 28, 2003.

(51) Int. Cl.
*A61B 17/56* (2006.01)

(52) U.S. Cl. ...................................................... 606/67

(58) Field of Classification Search ............. 623/11.11, 623/16.11, 22.11, 22.12; 606/67, 65, 60–62, 606/72–73, 75, 105, 32
See application file for complete search history.

(56) References Cited

U.S. PATENT DOCUMENTS

| | | | |
|---|---|---|---|
| 4,858,601 A | | 8/1989 | Glisson |
| 4,959,064 A | | 9/1990 | Engelhardt |
| 4,963,144 A | * | 10/1990 | Huene .......................... 606/73 |
| 5,370,646 A | | 12/1994 | Reese et al. |
| 5,993,459 A | * | 11/1999 | Larsen et al. ................ 606/104 |
| 6,004,327 A | | 12/1999 | Asnis et al. |
| 6,579,293 B1 | | 6/2003 | Chandran |
| 6,582,453 B1 | | 6/2003 | Tran et al. |
| 6,585,730 B1 | | 7/2003 | Foerster |
| 6,585,740 B2 | | 7/2003 | Schlapfer |
| 6,589,249 B2 | | 7/2003 | Sater et al. |
| 6,599,297 B1 | | 7/2003 | Carlsson et al. |

* cited by examiner

*Primary Examiner*—Alvin J. Stewart
(74) *Attorney, Agent, or Firm*—Knobbe Martens Olson & Bear LLP

(57) ABSTRACT

The invention relates to a deployment systems for deploying a bone fixation device. One embodiment of a deployment system includes a syringe-shaped body configured to provide proximal traction to a bone fixation device in response to a compressive force between a finger grip and a plunger adapted to be engaged by the heel of a clinician's hand. The device may include a collet for gripping a proximal pin of a fixation device. The deployment device may also include a tool that includes an elongate body with a distal tip adapted to rotationally engage a bone fixation device in order to axially rotate the fixation device. A further deployment device embodiment includes a cauterizing tip for heat-cutting an excess portion of a pin of a bone fixation device.

20 Claims, 19 Drawing Sheets

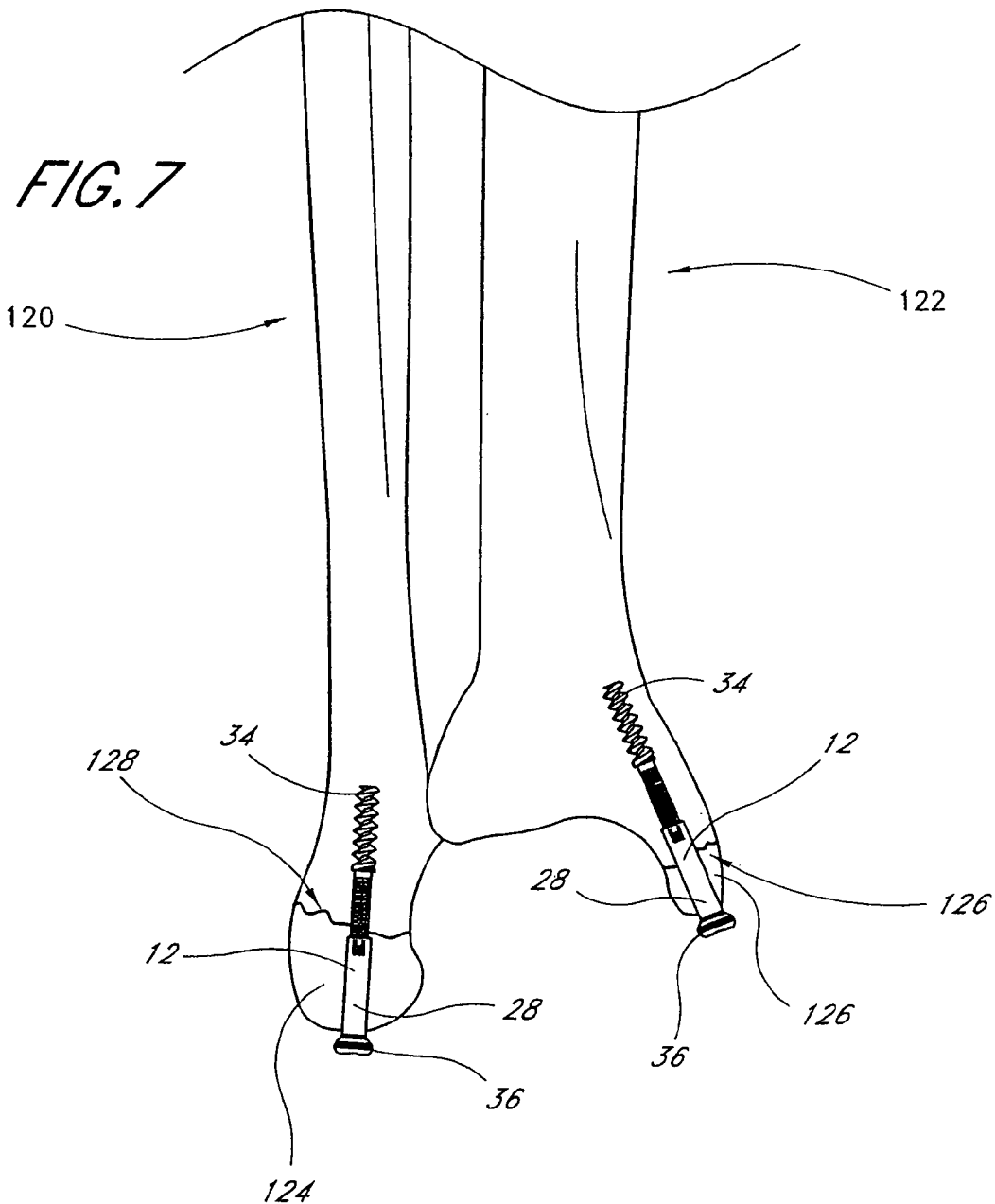

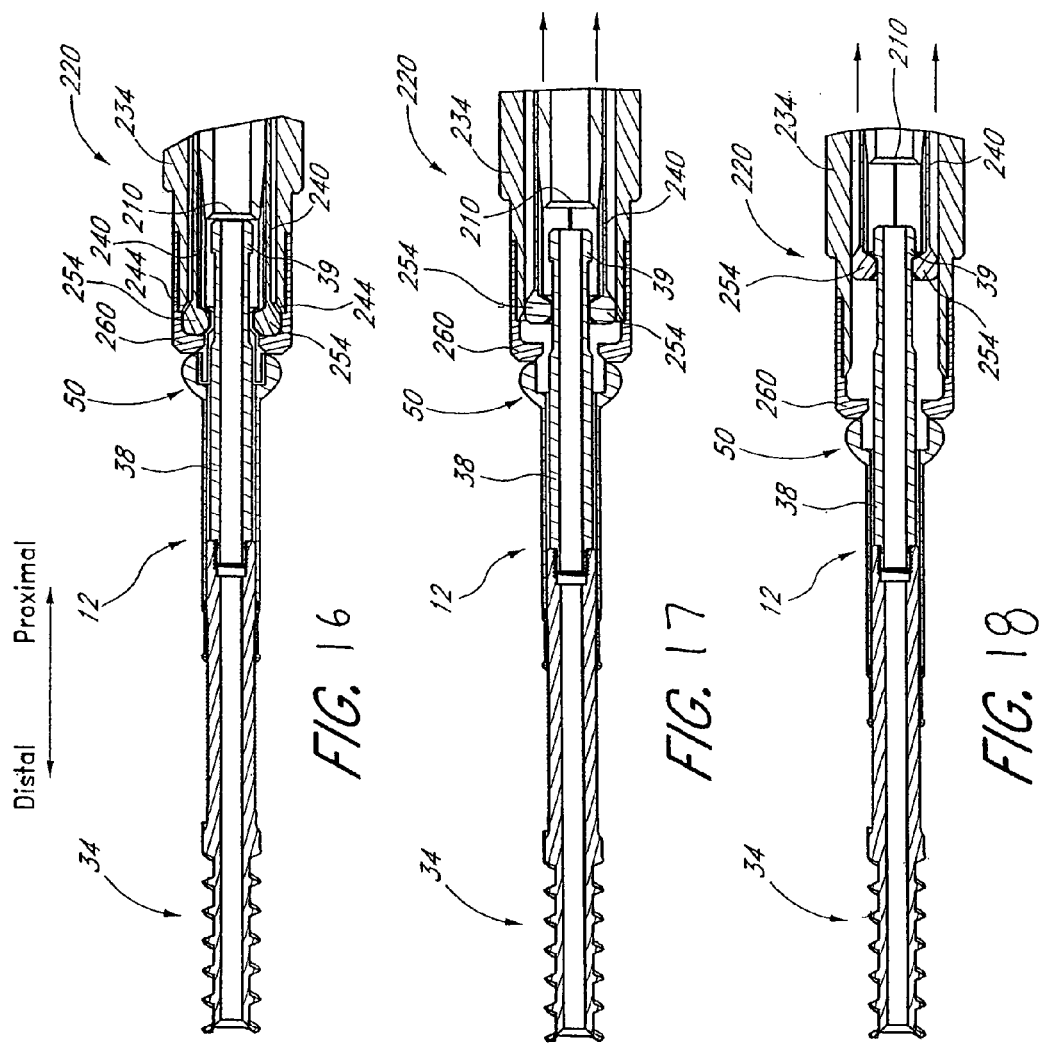

DEPLOYMENT TOOL FOR DISTAL BONE ANCHORS WITH SECONDARY COMPRESSION

RELATED APPLICATIONS

This application is a continuation-in-part of U.S. patent application Ser. No. 09/991,367, filed Nov. 13, 2001, now U.S. Pat. No. 6,890,333, which is a continuation-in-part of U.S. patent application Ser. No. 09/934,467, filed Aug. 23, 2001, now U.S. Pat. No. 6,511,481, issued Jan. 28, 2003 and this application claims the priority benefit under 35 U.S.C. § 119(e) of Provisional Patent Application 60/451,296 filed Feb. 28, 2003 and Provisional Patent Application 60/464,398 filed Apr. 21, 2003, both of which are hereby incorporated by reference in their entirety.

BACKGROUND

1. Field of the Invention

The invention relates in general to the field of bone anchors, and specifically to a deployment device for a bone anchor.

2. Description of the Related Art

The femur, otherwise known as the thigh bone, generally comprises an elongate shaft extending from the hip to the knee. The proximal end of the shaft includes a head, a neck, a greater trochanter and a lesser trochanter. The head of the femur fits into the acetabular cup of the hip bone to form a ball and socket joint at the hip. The distal end of the femur includes a medial condyle and a lateral condyle. The condyles engage an upper end of the tibia to form the knee joint. Overall, the femur is the longest and strongest bone in the skeleton. However, portions of the femur are extremely susceptible to fracturing.

Pertrochanteric fractures among geriatric patients are the most frequent in connection with those of the region of the neck of the bone. The advanced age and the pathologies which are encountered in these patients make a timely stabilization of skeletal injuries necessary in order to reduce to a minimum the bed confinement and the rehabilitation times. Preferably, devices and procedures are utilized which minimize complications brought about by the so-called immobilization syndrome, which may be lethal for patients in delicate metabolical circumstances. It is also preferable to reduce to a minimum blood losses related to surgical intervention. At the same time, the syntheses means utilized must be stable in order to allow the patient to very timely assume a seated position and, two or three days following the intervention, to reassume an erect posture with progressive bearing of weight.

Internal fixation of femoral fractures in general is one of the most common orthopedic surgical procedures. Fractures of the femur occur in both the proximal portion of the femur and the distal portion of the femur. Fractures of the proximal portion of the femur (hip fractures) are generally classified as femoral neck fractures, intertrochanteric fractures and subtrochanteric fractures. Fractures of the distal portion of the femur (knee fractures) are referred to as supracondylar fractures. Supracondylar fractures generally extend vertically between the condyles at the lower end of the femur to separate the distal portion of the femur into two main bone fragments. A fracture line may be further comminuted to create a plurality of smaller bone fragments. Fractures of the femur which extend into the neck of the bone are generally more difficult to treat than fractures restricted to the shaft of the femur.

Operative treatment of the fractures requires that the fractures be internally fixed and possibly compressed. Fractures of the neck, head or trochanters of the femur have been treated with a variety of compression screw assemblies which include generally a compression plate having a barrel member, a lag screw and a compressing screw. The compression plate is secured to the exterior of the femur and the barrel member is inserted into a predrilled hole in the direction of the femoral head. The lag screw which has a threaded end and a smooth portion is inserted through the barrel member so that it extends across the break and into the femoral head. The threaded portion engages the femoral head. The compressing screw connects the lag screw to the plate. By adjusting the tension of the compressing screw the compression (reduction) of the fracture can be adjusted.

A variety of elongated implants (nail, screw, pin, etc.) have been developed, which are adapted to be positioned along the longitudinal axis of the femoral neck with a leading (distal) end portion in the femoral head so as to stabilize a fracture of the femoral neck. The elongated implant may be implanted by itself or connected to another implant such as a side plate or intramedullary rod. The leading end portion of the implant typically includes means to positively grip the femoral head bone (external threads, expanding arms, etc.), but the inclusion of such gripping means can introduce several significant problems. First, implants with sharp edges on the leading end portion, such as the externally threaded implants, exhibit a tendency to migrate proximally towards the hip joint weight bearing surface after implantation. This can occur when the proximal cortical bone has insufficient integrity to resist distal movement of the screw head. Such proximal migration under physiological loading, which is also referred to as femoral head cut-out, can lead to significant damage to the adjacent hip joint. Also, the externally threaded implants can generate large stress concentrations in the bone during implantation which can lead to stripping of the threads formed in the bone and thus a weakened grip. The movable arms of known expanding arm devices are usually free at one end and attached at the other end to the main body of the leading end portion of the implant. As a result, all fatigue loading is concentrated at the attached ends of the arms and undesirably large bending moments are realized at the points of attachment. In addition, conventional threaded implants generally exhibit insufficient holding power under tension, such that the threads can be stripped out of the femoral head either by over-tightening during the implantation procedure or during post operative loading by the patient's weight.

Thus, notwithstanding the variety of efforts in the prior art, there remains a need for a deployment device for an orthopedic fixation device with improved locking force such as within the femoral head in a femoral neck application.

SUMMARY

In one embodiment, a method of securing a first bone fragment to a second bone fragment comprises forming a bore through the first bone fragment in the direction of the second bone fragment. A fixation device is advanced though the first bone fragment. The fixation device comprises an elongate body, having a proximal end and a distal end, a helical anchor on the distal end of the elongate body and a proximal anchor, moveably carried by the elongate body. The elongate body and the proximal anchor have complementary retention structures configured to resist proximal movement of the proximal anchor with respect to the elongate body. The fixation device is rotated to engage bone in the second bone fragment. A deployment device is used to apply a distal force to proximally withdraw the elongate body with respect to the proximal anchor.

In one embodiment, a deployment device for use with a bone fixation device is provided. The deployment device generally includes an elongate body with proximal and distal ends. A housing is disposed at the distal end, and has a traction member slidably disposed therein. The device also includes a plunger disposed a the proximal end, and a central portion between the housing and the plunger. The elements are assembled such that distal movement of the plunger relative to the central portion results in proximal motion of the traction member relative to the housing.

According to another embodiment, a deployment device includes an elongate proximal housing having a proximal end and a distal end, and an elongate distal housing extending distally from the distal end of the proximal housing. The device further includes a finger grip movably disposed along the proximal housing, a plunger attached to the proximal end of the proximal housing, and a tensioner extending through the distal and proximal housings. The tensioner is adapted to grip a proximal end of a bone fixation device. The elements are assembled such that a compressive force between the finger grip and the plunger portion causes proximal movement of the tensioner relative to the distal housing. In another embodiment, the tensioner comprise a pin adapted to engage a bone fixation device.

In another embodiment, a syringe-shaped deployment device for use with a bone fixation device is provided. The deployment device comprises a plunger disposed at a proximal end and a finger engagement portion disposed distally from the plunger. The finger engagement portion is free to move axially relative to the plunger. Additionally, the device includes an elongate housing disposed distally from the finger engagement portion. The elongate housing is adapted to move with the plunger relative to the finger engagement portion. The device also includes a tensioner within the housing adapted to move with the finger engagement portion relative to the plunger and the housing. The tensioner is adapted to grip a proximal pin of a bone fixation device. In another embodiment, the tensioner and a proximal pin form an integral body to engage a bone fixation device.

In still another embodiment, a bone anchor deployment device includes an elongate body having a handle at a proximal end and a distal tip. The distal tip is configured to engage a proximal flange of a proximal bone anchor such that rotation of the deployment device results in rotation of the bone anchor. In this embodiment, distal tip comprises a hexagonal shape with a central hole configured to receive a proximal pin of a bone anchor. The pin may be received in the central hole until it abuts a stop at a pre-determined depth within the hole.

In yet another embodiment, a bone fixation device and deployment system is described. The system includes a bone fixation device comprising an elongate body having a proximal end and a distal end and comprising a first portion and a second portion which are detachably coupled to each other at a junction. The fixation device further includes a helical anchor on the distal end, a retention structure on the body proximal to the anchor, and an anti-rotational structure on the first portion of the body. The fixation device also includes a proximal anchor, movably carried by the body and comprising a tubular sleeve that in a first position extends distally past the junction between the first portion the second portion. The proximal anchor also has a rotational coupling. The proximal anchor is movable in the distal direction with respect to the body, the retention structure resists proximal movement of the proximal anchor with respect to the body and the anti-rotational structure prevents rotational movement of the first portion of the body with respect to the proximal anchor. The system further includes a deployment device comprising an elongate body having a distal end configured to engage the rotational coupling of the proximal anchor.

For purposes of summarizing the invention and the advantages achieved over the prior art, certain objects and advantages of the invention have been described herein above. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

All of these embodiments are intended to be within the scope of the present invention herein disclosed. These and other embodiments of the present invention will become readily apparent to those skilled in the art from the following detailed description of the preferred embodiments having reference to the attached figures, the invention not being limited to any particular preferred embodiment(s) disclosed.

BRIEF DESCRIPTION OF DRAWINGS

Having thus summarized the general nature of the invention, certain preferred embodiments and modifications thereof will become apparent to those skilled in the art from the detailed description herein having reference to the figures that follow, of which:

FIG. 7 is an anterior view of the distal tibia and fibula, with fixation devices similar to that of FIG. 1 arranged across lateral and medial malleolar fractures.

FIG. 16 is a section view illustrating a first step of a method of deploying a bone fixation device.

FIG. 17 is a section view illustrating a second step of a method of deploying a bone fixation device.

FIG. 18 is a section view illustrating a third step of a method of deploying a bone fixation device.

DETAILED DESCRIPTION

Figure 1:
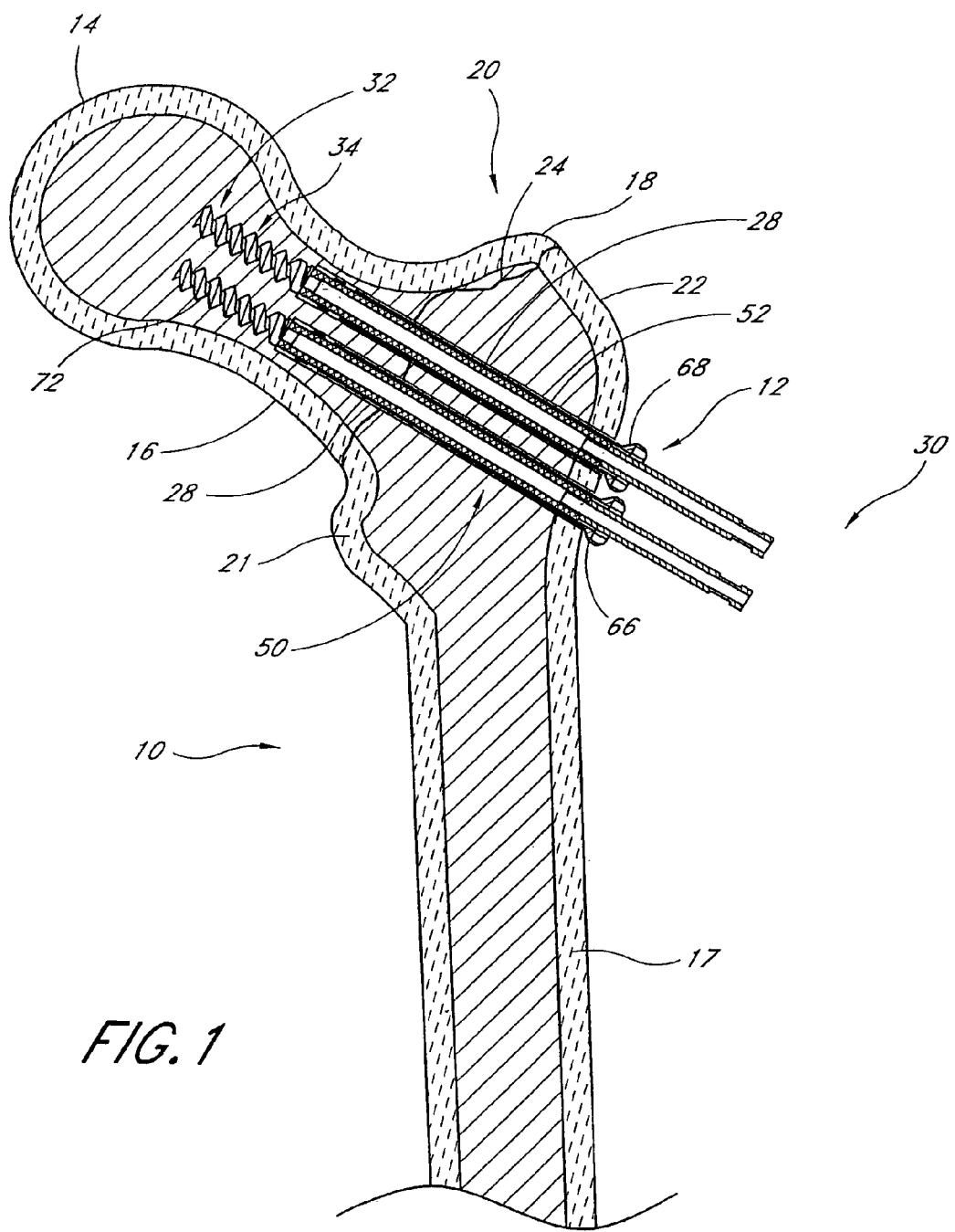
FIG. 1 is a posterior elevational posterior cross section through the proximal portion of the femur, illustrating two femoral neck fracture fixation devices positioned therein.

Although the fixation devices of the present invention will be disclosed primarily in the context of fractures of the proximal femur, the methods and structures disclosed herein are intended for application in any of a wide variety of bones and fractures, as will be apparent to those of skill in the art in view of the disclosure herein. For example, the bone fixation device of the present invention is applicable in a wide variety of fractures and osteotomies in the hand, such as interphalangeal and metacarpophalangeal arthrodesis, transverse phalangeal and metacarpal fracture fixation, spiral phalangeal and metacarpal fracture fixation, oblique phalangeal and metacarpal fracture fixation, intercondylar phalangeal and metacarpal fracture fixation, phalangeal and metacarpal osteotomy fixation as well as others known in the art. A wide variety of phalangeal and metatarsal osteotomies and fractures of the foot may also be stabilized using the bone fixation device of the present invention. These include, among others, distal metaphyseal osteotomies such as those described by Austin and Reverdin-Laird, base wedge osteotomies, oblique diaphyseal, digital arthrodesis as well as a wide variety of others that will be known to those of skill in the art. The bone fixation device may be used with or without plate(s) or washer(s), all of which can be either permanent, absorbable, or combinations.

Fractures of the fibular and tibial malleoli, pilon fractures and other fractures of the bones of the leg may be fixated and stabilized with the present invention with or without the use of plates, both absorbable or non-absorbing types, and with alternate embodiments of the current invention. Fractures and osteotomies of the mid and hind foot, tarsal arthrodesis and osteotomy, or others as are known to those with skill in the art. One example is the fixation of the medial malleolar avulsion fragment.

The fixation device of the present invention may also be used to attach tissue or structure to the bone, such as in ligament reattachment and other soft tissue attachment procedures. Plates and washers, with or without tissue spikes for soft tissue attachment, and other implants may also be attached to bone, using either resorbable or nonresorbable fixation devices depending upon the implant and procedure. The fixation device may also be used to attach sutures to the bone, such as in any of a variety of tissue suspension procedures.

For example, peripheral applications for the fixation devices include utilization of the device for fastening soft tissue such as capsule, tendon or ligament to bone. It may also be used to attach a synthetic material such as marlex mesh, to bone or allograft material such as tensor fascia lata, to bone. In the process of doing so, retention of the material to bone may be accomplished with the collar as shown, or the pin and or collar may be modified to accept a suture or other material for facilitation of this attachment.

Specific examples include attachment of the posterior tibial tendon to the navicular bone in the Kidner operation. This application may be accomplished using an appropriately sized implant of the present invention along with a washer with distally extending soft tissue spikes. Navicular-cuneiform arthrodesis may be performed utilizing the device and concurrent attachment of the tendon may be accomplished. Attachment of the tendon may be accomplished in the absence of arthrodesis by altering the placement of the implant in the adjacent bone.

Ligament or capsule reattachment after rupture, avulsion or detachment, such as in the ankle, shoulder or knee can also be accomplished using the devices disclosed herein.

The fixation devices may be used in combination with semi tubular, one-third tubular and dynamic compression plates, both of metallic and absorbable composition, if the collar is modified to match the opening on the plate.

The canulated design disclosed below can be fashioned to accept an antibiotic impregnated rod for the slow adsorption of medication locally. This may be beneficial for prophylaxis, especially in open wounds, or when osteomyelitis is present and stabilization of fracture fragments is indicated.

A kit may be assembled for field use by military or sport medical or paramedical personnel. This kit contains an implanting tool, and a variety of implant device size and types. The kit may include additional components such as sterilization or disinfectant materials, a skin stapler, bandages, gloves, and basic tools for emergent wound and fracture treatment. Antibiotic rods may be included for wound prophylaxis during transport.

Referring to FIG. 1, there is illustrated a posterior side elevational view of the proximal portion of a femur 10, having a fixation device 12 positioned therein. The proximal end of the femur 10 comprises a head 14 connected by way of a neck 16 to the long body or shaft 17 of the femur 10. As illustrated in FIG. 1, the neck 16 is smaller in diameter than the head 14. The neck 16 and head 14 also lie on an axis which, on average in humans, crosses the longitudinal axis of the body 17 of the femur 10 at an angle of about 126°. The risk of fracture at the neck 16 is thus elevated, among other things, by the angular departure of the neck 16 from the longitudinal axis of the body 17 of femur 10 and also the reduced diameter of the neck 16 with respect to the head 14.

The greater trochanter 18 extends outwardly above the junction of the neck 16 and the body 17 of the femur 10. On the medial side of the greater trochanter 18 is the trochanteric fossa 20. This depression accommodates the insertion of the obturator externus muscle. The lesser trochanter 21 is located posteromedially at the junction of the neck 16 and the body 17 of the femur 10. Both the greater trochanter 18 and the lesser trochanter 21 serve for the attachment of muscles. On the posterior surface of the femur 10 at about the same axial level as the lesser trochanter 21 is the gluteal tuberosity 22, for the insertion of the gluteus maximus muscle. Additional details of the femur are well understood in the art and not discussed in further detail herein.

FIG. 1 illustrates a fracture 24 which crosses the femur approximately in the area of the greater trochanter 18. Fractures of the proximal portion of the femur 10 are generally classified as capital or subcapital femoral neck fractures, and intertrochanteric fractures. All of these fractures will be deemed femoral neck fractures for the purpose of describing the present invention.

Referring to FIGS. 1-4, the fixation device 12 comprises a body 28 extending between a proximal end 30 and a distal end 32. The length, diameter and construction materials of the body 28 can be varied, depending upon the intended clinical application. In embodiments optimized for various fractures in an adult human population, the body 28 will generally be within the range of from about 10 mm to about 150 mm in length after sizing, and within the range of from about 2 mm to about 8 mm in maximum diameter. The major diameter of the helical anchor, discussed below, may be within the range of from about 2.7 mm to about 12 mm. In general, the appropriate dimensions of the body 28 will vary, depending upon the specific fracture. In rough terms, for a malleolar fracture, shaft diameters in the range of from about 3 mm to about 4.5 mm may be used, and lengths within the range of from about 25 mm to about 70 mm. For condylar fractures, shaft diameters within the range of from about 3.5 mm to about 6.5 mm may be used with lengths within the range of from about 25 mm to about 70 mm. For colles fractures (distal radius and ulna), diameters within the range of from about 2.0 mm to about 4.5 mm may be used with any of a variety of lengths within the range of from about 6 mm to about 70 mm.

In one embodiment, the body 28 comprises titanium. However, as will be described in more detail below, other metals or bioabsorbable or nonabsorbable polymeric materials may be utilized, depending upon the dimensions and desired structural integrity of the finished fixation device 12.

The distal end 32 of the body 28 is provided with a cancellous bone anchor or distal cortical bone anchor 34. Additional details of the distal bone anchor are described below. In general, in a femoral neck application, distal bone anchor 34 is adapted to be rotationally inserted into the cancellous bone within the head 14 of the femur 10, to retain the fixation device 12 within the femoral head.

Figure 3:
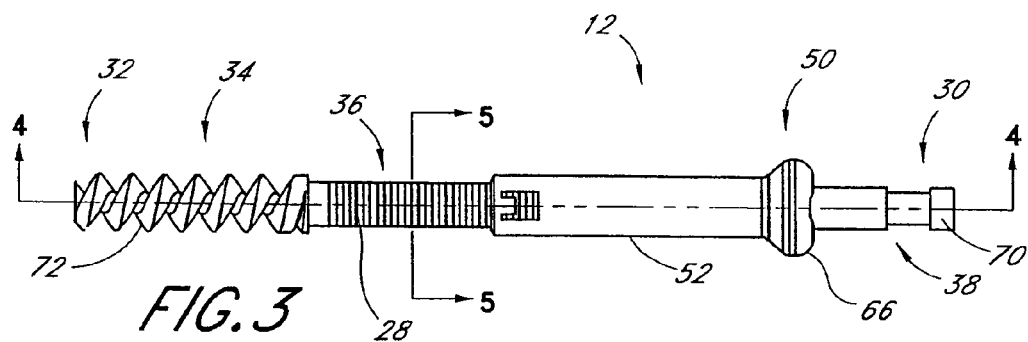
FIG. 3 is a side elevational view of the fixation device of FIG. 2.
Figure 4:
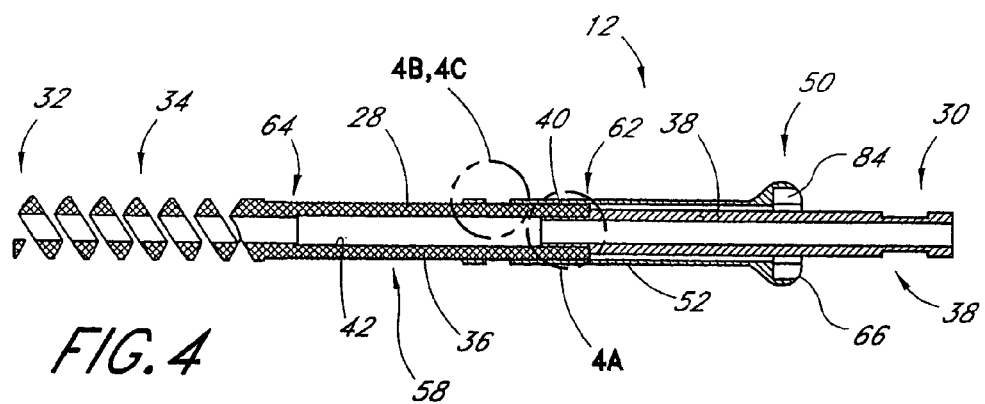
FIG. 4 is a cross-sectional view taken through line 4-4 of FIG. 3.
Figure 4A:
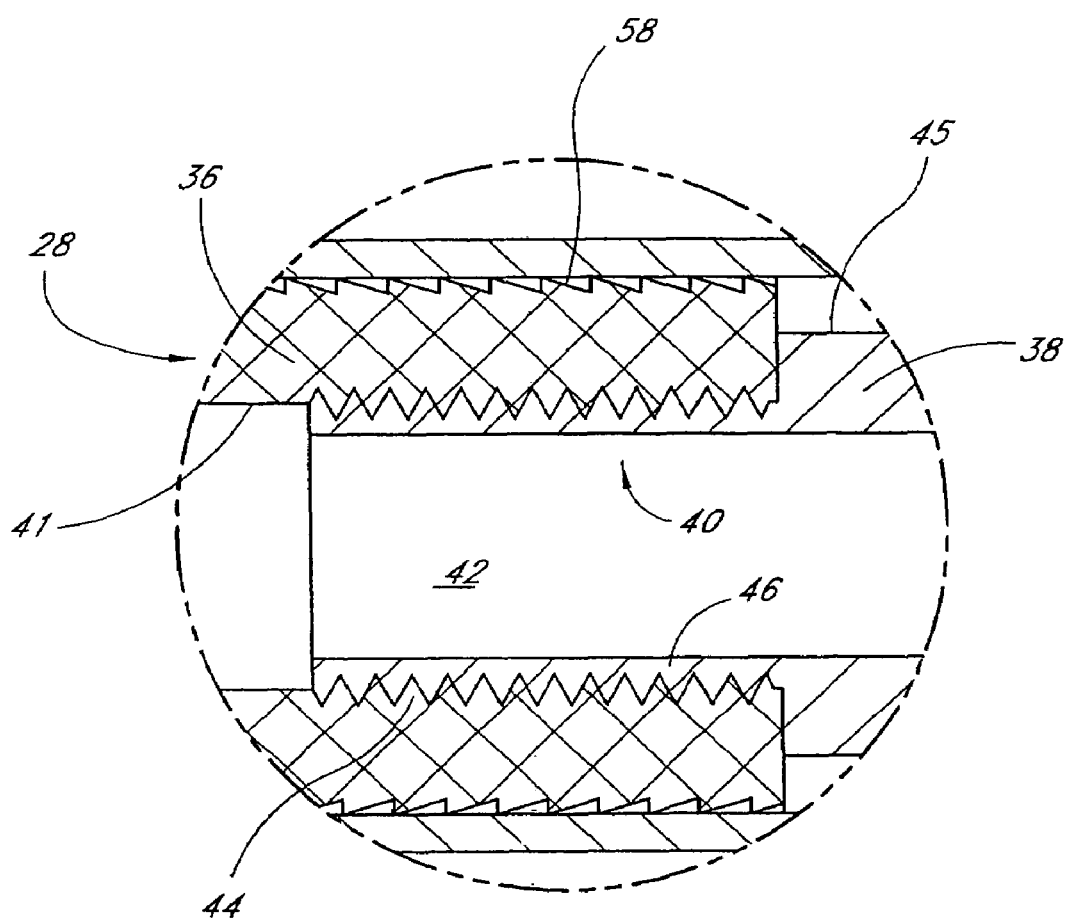
FIG. 4A is an enlarged view of portion 4A of FIG. 4.

Referring to FIGS. 3, 4, and 4A, the body 28 comprises a first portion 36 and a second portion 38 that are coupled together at a junction 40. In the illustrated embodiment, the first portion 36 carries the distal anchor 34 while the second portion 38 forms the proximal end 30 of the body 28. The first and second portions 36, 38 are preferably detachably coupled to each other at the junction 40. In the illustrated embodiment, the first and second portions 36, 38 are detachably coupled to each other via interlocking threads. Specifically, as best seen in FIG. 4A, the body 28 includes an inner surface 41, which defines a central lumen 42 that preferably extends from the proximal end 30 to the distal end 32 throughout the body 28. At the proximal end of the first portion 36, the inner surface 41 includes a first threaded portion 44. The first threaded portion 44 is configured to mate with a second threaded portion 46, which is located on the outer surface 45 of the second portion 38. The interlocking annular threads of the first and second threaded portions 44, 46 allow the first and second portions 36, 38 to be detachably coupled to each other. In one modified embodiment, the orientation of the first and second threaded portions 44, 46 can be reversed. That is, the first threaded portion 44 can be located on the outer surface of the first portion 36 and the second threaded portion 46 can be located on the inner surface 41 at the distal end of the second portion 38. Any of a variety of other releasable complementary engagement structures may also be used, to allow removal of second portion 38 following implantation, as is discussed below.

In a modified arrangement, the second portion 38 can comprise any of a variety of tensioning elements for permitting proximal tension to be placed on the distal anchor 34 while the proximal anchor is advanced distally to compress the fracture. For example, any of a variety of tubes or wires can be removably attached to the first portion 36 and extend proximally to the proximal handpiece. In one such arrangement, the first portion 36 can include a releasable connector in the form of a latching element, such as an eye or hook. The second portion 38 can include a complementary releasable connector (e.g., a complementary hook) for engaging the first portion 36. In this manner, the second portion 38 can be detachably coupled to the first portion 36 such proximal traction can be applied to the first portion 36 through the second portion as will be explained below. Alternatively, the second portion 48 may be provided with an eye or hook, or transverse bar, around which or through which a suture or wire may be advanced, both ends of which are retained at the proximal end of the device. Following proximal tension on the tensioning element during the compression step, one end of the suture or wire is released, and the other end may be pulled free of the device. Alternate releasable proximal tensioning structures may be devised by those of skill in the art in view of the disclosure herein.

The proximal end 30 of the fixation device is provided with a proximal anchor 50. Proximal anchor 50 is axially distally moveable along the body 28, to permit compression of the fracture 24 as will be apparent from FIG. 1 and the description below. As will be explained below, complimentary locking structures such as threads or ratchet like structures between the proximal anchor 50 and the body 28 resist proximal movement of the anchor 50 with respect to the body 28 under normal use conditions. The proximal anchor 50 preferably can be axially advanced along the body 28 without rotation as will be apparent from the disclosure herein.

In the illustrated embodiment, proximal anchor 50 comprises a housing 52 such as a tubular body, for coaxial movement along the body 28. As best seen in FIGS. 1 and 4, in a final position, the housing 52 extends distally past the junction 40 between the first portion 36 and the second portion 38. The housing 52 is provided with one or more surface structures 54 such as a radially inwardly projecting flange 56 (see FIGS. 4B and 4C), for cooperating with complementary surface structures 58 on the first portion 36 of the body 28. In the illustrated embodiment, the complimentary surface structures 58 comprise a series of annular ridges or grooves 60. The surface structures 54 and complementary surface structures 58 permit distal axial travel of the proximal anchor 50 with respect to the body 28, but resist proximal travel of the proximal anchor 50 with respect to the body 28.

Figure 4B:
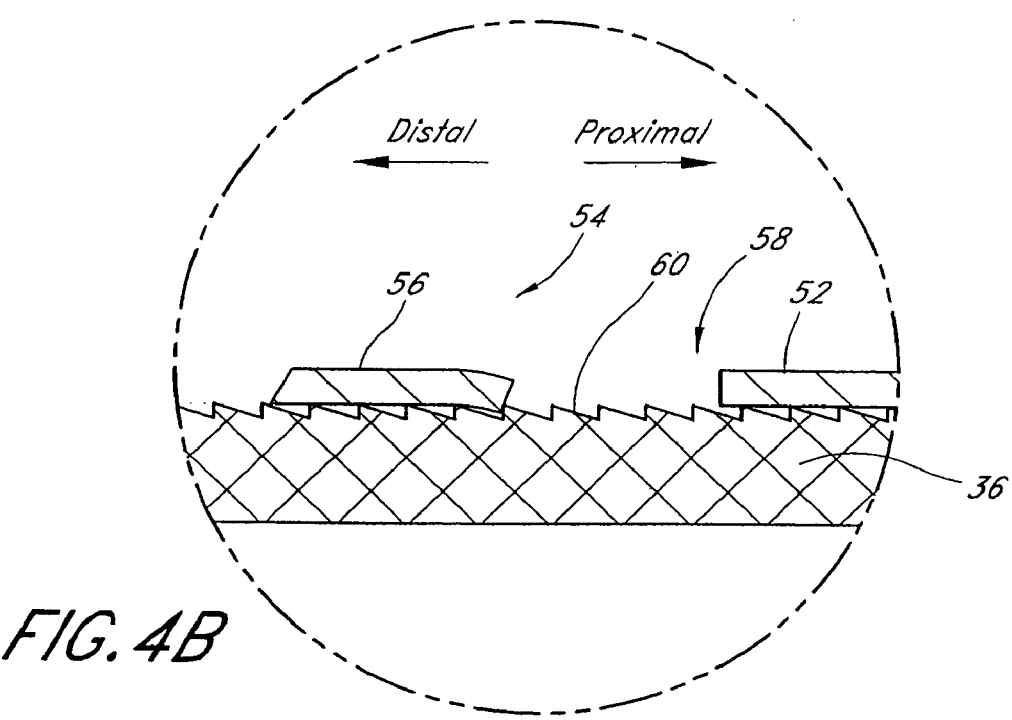
FIG. 4B is an enlarged view of portion 4B of FIG. 4 with the fixation device in a first position.
Figure 4C:
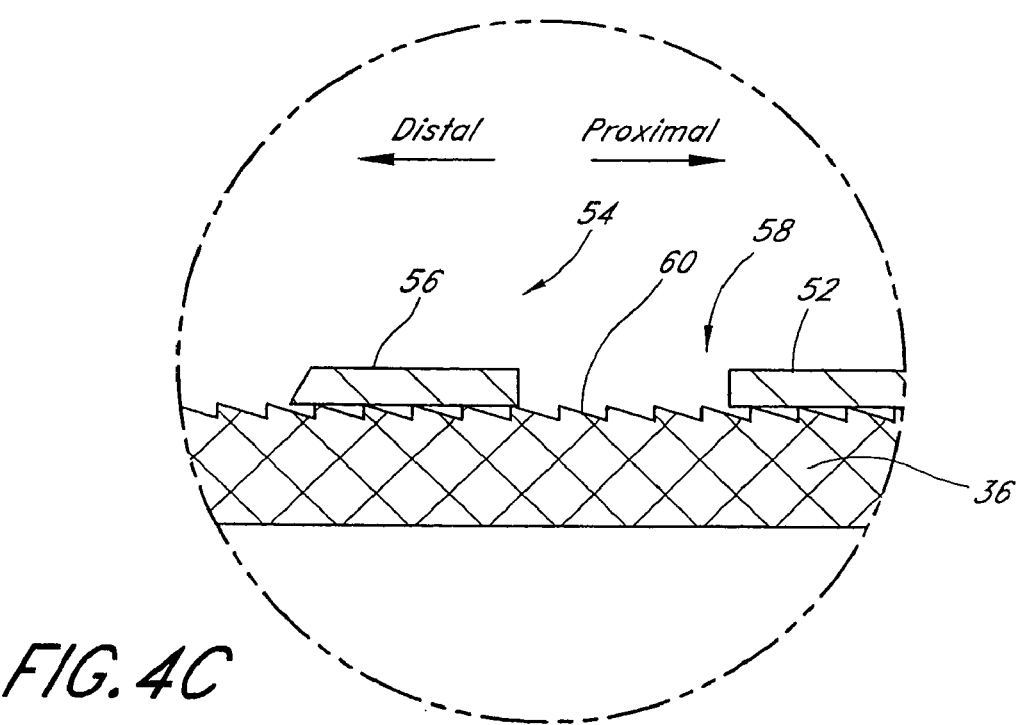
FIG. 4C is an enlarged view of portion 4C of FIG. 4 with the fixation device in a second position.

For example, as best seen in FIG. 4B, the proximal end of the flange 56 is biased towards the longitudinal axis of the body 28. As such, when the proximal anchor 50 is urged proximally with respect to the body 28, the flange 56 engages the grooves or ridges 60 of the complementary surface structures 58. This prevents proximal movement of the proximal anchor 50 with respect to the body 28. In contrast, as best seen in FIG. 4C, when the proximal anchor 50 is moved distally with respect to the body 28, the flange 56 can bend outwardly away from the body 28 and the ridges 60 so as to allow the proximal anchor 50 to move distally. Of course, those of skill in the art will recognize that there are a variety of other complementary surface structures, which permit one way ratchet like movement. For example, a plurality of annular rings or helical threads, ramped ratchet structures and the like for cooperating with an opposing ramped structure or pawl can also be used. In one embodiment, opposing screw threads are dimensioned to function as a ratchet.

Retention structures 58 are spaced axially apart along the body 28, between a proximal limit 62 and a distal limit 64. The axial distance between proximal limit 62 and distal limit 64 is related to the desired axial working range of the proximal anchor 50, and thus the range of functional sizes of the fixation device 12. Thus, the present invention provides a bone fixation device which can provide compression across a fracture throughout a range of motion following the placement of the distal anchor. The distal anchor may be positioned within the cancellous and/or distal cortical bone, and the proximal anchor may be distally advanced throughout a range to provide compression across the fracture without needing to relocate the distal anchor and without needing to initially locate the distal anchor in a precise position with respect to the proximal side of the bone. Providing a working range throughout which tensioning of the proximal anchor is independent from setting the distal anchor allows a single device to be useful for a wide variety of fractures, as well as eliminates the need for accurate device measurement and accurate placement of the distal anchor. In many applications, the working range is at least about 10% of the overall length of the device, and may be as much as 20% or 30% or more of the overall device length. In the context of a femoral application, working ranges of up to about 10 mm or more may be provided, since estimates within that range can normally be readily accomplished within the clinical setting. In other applications, such as a metatarsal fracture, a working range in the area of from about 1 mm to about 2 mm may be all that is necessary. The embodiments disclosed herein can be scaled to have a greater or a lesser working range, as will be apparent to those of skill in the art in view of the disclosure herein. Additional embodiments of the proximal anchor are disclosed in U.S. Pat. No. 6,685,706, issued Feb. 3, 2004, entitled "PROXIMAL ANCHORS FOR BONE FIXATION SYSTEM", which is hereby incorporated by reference in its entirety herein.

The proximal anchor 50 includes a flange 66 that seats against the outer surface of the femur or tissue adjacent the femur. The flange 66 is preferably an annular flange, to optimize the footprint or contact surface area between the flange 66 and the femur. Circular or polygonal shaped flanges for use in femoral head fixation will generally have a diameter of at least about 4 mm greater than the adjacent body 28 and often within the range of from about 4 mm to about 20 mm or more greater than the adjacent body 28.

In the illustrated embodiment, the bone contacting surface 68 of the flange 44 is tapered and generally faces the shaft 17 of the femur 10. In other embodiments, the bone contacting surface 69 can resides in or approximately on a plane, which is perpendicular with respect to the longitudinal axis of the body 28. In other embodiments, other angular relationships between the bone contacting surface 68 of the flange 66 and the longitudinal axis of the body 28 and housing 52 may be utilized, depending upon the anticipated entrance angle of the body 28 and associated entrance point surface of the femur 10. In general, the longitudinal axis extending through the head 14 and neck 16 of the human femur is inclined at an angle of approximately 126° from the longitudinal axis of the long body 17 of the femur 10. Angles between the longitudinal axis of body 28 and tissue contacting surface 68 within the range of from about 90° to about 140° will generally be utilized.

In a modified embodiment, the housing 52 of the proximal anchor 50 can include one or more one or more barbs that extend radially outwardly from the tubular housing 52. Such barbs provide for self tightening after the device has been implanted in the patient as described in a co-pending U.S. Patent Application entitled "DISTAL BONE FOR BONE FIXATION WITH SECONDARY COMPRESSION", application Ser. No. 10/012,687, filed Nov. 13, 2001, which is hereby expressly incorporated by reference herein. The barbs may be radially symmetrically distributed about the longitudinal axis of the housing 52. Each barb is provided with a transverse engagement surface, for anchoring the proximal anchor 50 in the bone. The transverse engagement surface may lie on a plane which is transverse to the longitudinal axis of the housing 50 or may be inclined with respect to the longitudinal axis of the tubular 50. In either arrangement, the transverse engagement surface 43 generally faces the bone contacting surface 68 of the flange 44. As such, the transverse engagement surface inhibits proximal movement of the proximal anchor with respect to the bone.

The clinician can be provided an array of proximal anchors 50 of varying angular relationships between the bone contacting surface 68 and the longitudinal axis of the body 28 and housing 52 (e.g., 90°, 100°, 110°, 120°, and 130°). A single body 28 can be associated with the array such as in a single sterile package. The clinician upon identifying the entrance angle of the body 28 and the associated entrance point surface orientation of the femur 10 can choose the anchor 50 from the array with the best fit angular relationship, for use with the body 28.

With particular reference to FIG. 3, the proximal end 30 of the body 28 may be provided with a rotational coupling 70, for allowing the second portion 38 of the body 28 to be rotationally coupled to a rotation device as will be described in more detail below with reference to FIGS. 9-20. The proximal end 30 of the body 28 may be desirably rotated to accomplish one or two discrete functions. In one application of the invention, the proximal end 30 is rotated to remove the second portion 38 of the body 28 following tensioning of the device across a fracture or to anchor an attachment to the bone. Rotation of the rotational coupling 70 may also be utilized to rotationally drive the distal anchor into the bone. Any of a variety of rotation devices may be utilized, such as electric drills or hand tools, which allow the clinician to manually rotate the proximal end 30 of the body. As mentioned above, certain preferred embodiments of hand tools will be described below with reference to FIGS. 9-20. Thus, the rotational coupling 70 may have any of a variety of cross sectional configurations, such as one or more flats or splines.

In one embodiment, the rotational coupling 70 comprises a proximal projection of the body 28 having an axial recess with a polygonal cross section, such as a hexagonal cross section. The rotational coupling 70 is illustrated as a female component, machined or milled or attached to the proximal end 30 of the body 28. However, the rotational coupling may also be in the form of a male element, such as a hexagonal or other noncircular cross sectioned projection.

As illustrated, the body 28 is cannulated to accommodate installation over a placement wire as is understood in the art. The cross section of the illustrated central cannulation is circular but in other embodiments may be non circular, e.g., hexagonal, to accommodate a corresponding male tool for installation or removal of the second portion 38 of the body 28 as will be explained below. In other embodiments, the body 28 may partially or wholly solid.

In all of the embodiments illustrated herein, the distal anchor 34 comprises a helical locking structure 72 for engaging cancellous and/or distal cortical bone. In the illustrated embodiment, the locking structure 72 comprises a flange that is wrapped around the axial lumen. The flange extends through at least one and generally from about two to about 50 or more full revolutions depending upon the axial length of the distal anchor and intended application. For most femoral neck fixation devices, the flange will generally complete from about 2 to about 20 revolutions. The helical flange 72 is preferably provided with a pitch and an axial spacing to optimize the retention force within cancellous bone, to optimize compression of the fracture.

The helical flange 72 of the illustrated embodiment has a generally triangular cross-sectional shape (see FIG. 4). However, it should be appreciated that the helical flange 72 can have any of a variety of cross sectional shapes, such as rectangular, oval or other as deemed desirable for a particular application through routine experimentation in view of the disclosure herein. The outer edge of the helical flange 72 defines an outer boundary. The ratio of the diameter of the outer boundary to the diameter of the central lumen can be optimized with respect to the desired retention force within the cancellous bone and giving due consideration to the structural integrity and strength of the distal anchor 34. Another aspect of the distal anchor 34 that can be optimized is the shape of the outer boundary and the central core, which in the illustrated embodiment are generally cylindrical.

The distal end 32 and/or the outer edges of the helical flange 72 may be atraumatic (e.g., blunt or soft). This inhibits the tendency of the fixation device 12 to migrate anatomically proximally towards the hip joint bearing surface after implantation (i.e., femoral head cut-out). Distal migration is also inhibited by the dimensions and presence of the proximal anchor 50, which has a larger footprint than conventional screws.

A variety of other arrangements for the distal anchor 32 can also be used. For example, the various distal anchors described in U.S. Pat. No. 6,511,481, issued Jan. 29, 2003, co-pending U.S. Patent Application entitled "DISTAL BONE FOR BONE FIXATION WITH SECONDARY COMPRESSION", application Ser. No. 10/012,687, filed Nov. 13, 2001 and co-pending U.S. Patent Application entitled "METHOD AND APPARATUS FOR BONE FIXATION WITH SECONDARY COMPRESSION", application Ser. No. 10/195,832, filed Jul. 12, 2002 can be incorporated into the fixation device 12 described herein. The entire contents these applications are hereby expressly incorporated by reference. In particular, the distal anchor may comprise a single helical thread surrounding a central core, much as in a conventional screw, which has been cannulated to facilitate placement over a wire. Alternatively, a double helical thread may be utilized, with the distal end of the first thread rotationally offset from the distal end of the second thread. The use of a double helical thread can enable a greater axial travel for a given degree of rotation and greater retention force than a corresponding single helical thread. Specific distal anchor designs can be optimized for the intended use, taking into account desired performance characteristics, the integrity of the distal bone, and whether the distal anchor is intended to engage exclusively cancellous bone or will also engage cortical bone.

Figure 2:
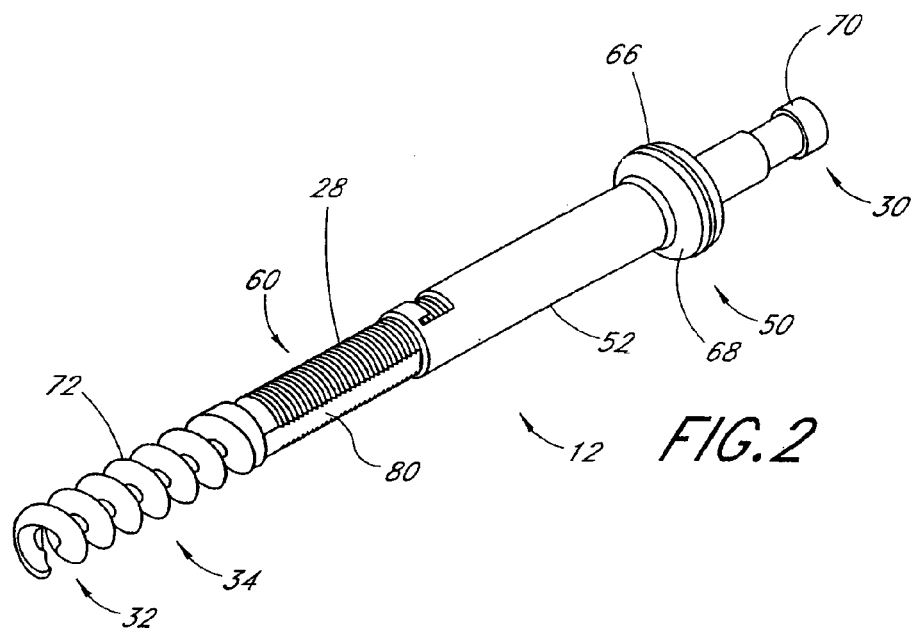
FIG. 2 is a side perspective view of a fixation device similar to that of FIG. 1.
Figure 5:
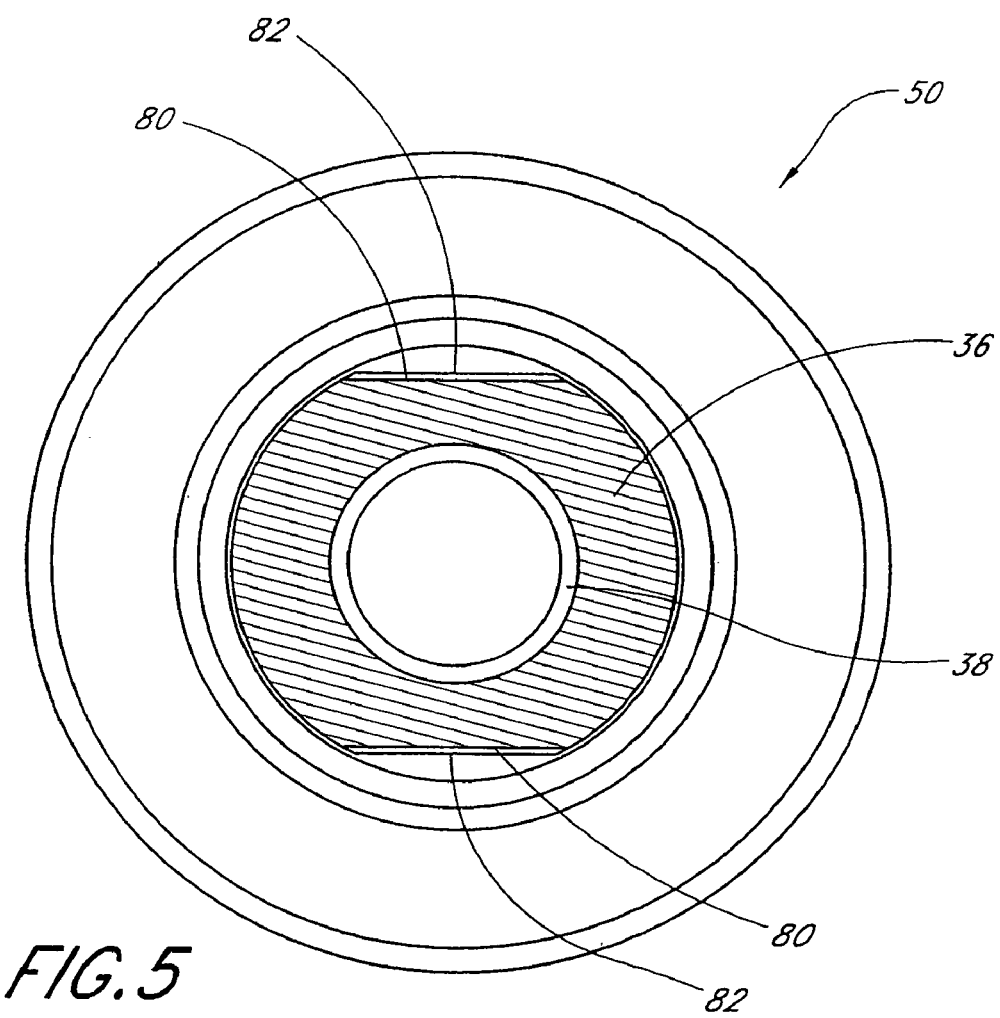
FIG. 5 is a cross-sectional view taken through line 5-5 of FIG. 3.

With particular reference to FIGS. 2 and 5, the fixation device may include an antirotation lock between the first portion 36 of the body 28 and the proximal collar 50. In the illustrated embodiment, the first portion 36 includes a pair of flat sides 80, which interact with corresponding flat structures 82 in the proximal collar 50. One or three or more axially extending flats may also be used. As such, rotation of the proximal collar 50 is transmitted to the first portion 36 and distal anchor 34 of the body 28. Of course, those of skill in the art will recognize various other types of splines or other interfit structures can be used to prevent relative rotation of the proximal anchor and the first portion 36 of the body 28.

To rotate the proximal collar, the flange 66 is preferably provided with a gripping structure to permit an insertion tool to rotate the flange 66. Any of a variety of gripping structures may be provided, such as one or more slots, flats, bores or the like. In one embodiment, the flange 44 is provided with a polygonal, and, in particular, a pentagonal or hexagonal recess 84 such that a similarly shaped and sized may engage the recess for rotation. See FIG. 4.

Figure 6A:
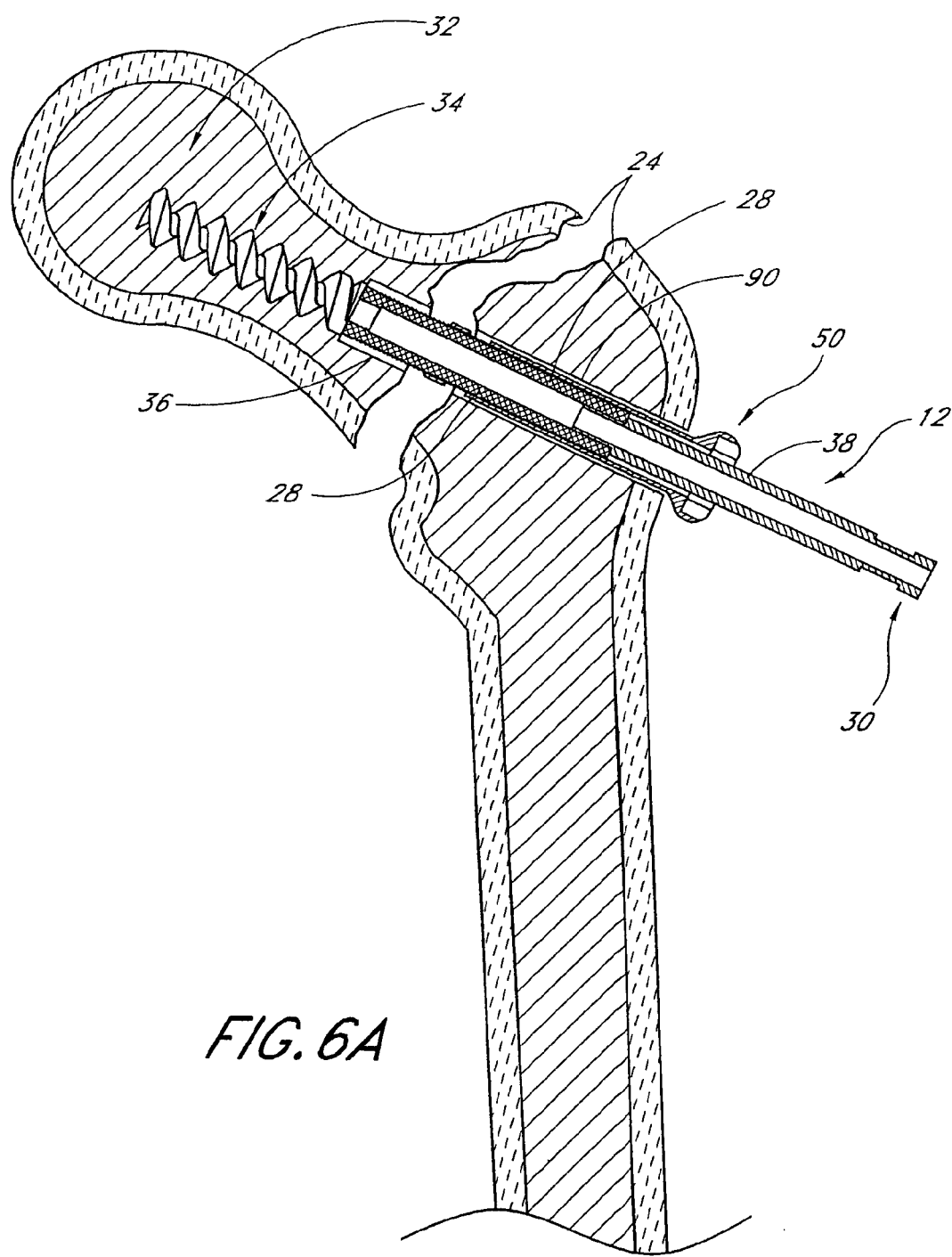
FIGS. 6A-C illustrate a procedure for using of the fixation device of FIG. 1 to secure a femoral neck fracture.

In use, the clinician first identifies a patient having a fracture to be treated, such as a femoral neck fracture, which is fixable by an internal fixation device. The clinician accesses the proximal femur, reduces the fracture if necessary and selects a bone drill and drills a hole 90 (see FIG. 6A) in accordance with conventional techniques. Frequently, the hole 90 has a diameter within the range from about 3 mm to about 8 mm. This diameter may be slightly larger than the diameter of the distal anchor 34. The hole 90 preferably extends up to or slightly beyond the fracture 24. Although not illustrated in FIGS. 6A-C, the hole 90 is preferably provided with a countersink such that the proximal anchor 50 sits flush or nearly flush against the outer surface of the bone.

A fixation device 12 having an axial length and outside diameter suitable for the hole 90 is selected. The distal end 32 of the fixation device 12 is advanced distally into the hole 90 until the distal anchor 34 reaches the distal end of the hole 90. The proximal anchor 50 may be carried by the fixation device 12 prior to advancing the body 28 into the hole 90, or may be attached following placement of the body 28 within the hole 90. Once the body 28 and proximal anchor 50 are in place, the clinician may use any of a variety of driving devices, such as electric drills or hand tools (e.g., the embodiments described below) to rotate the proximal anchor 50 and thus cancellous bone anchor 34 into the head of the femur.

Figure 6B:
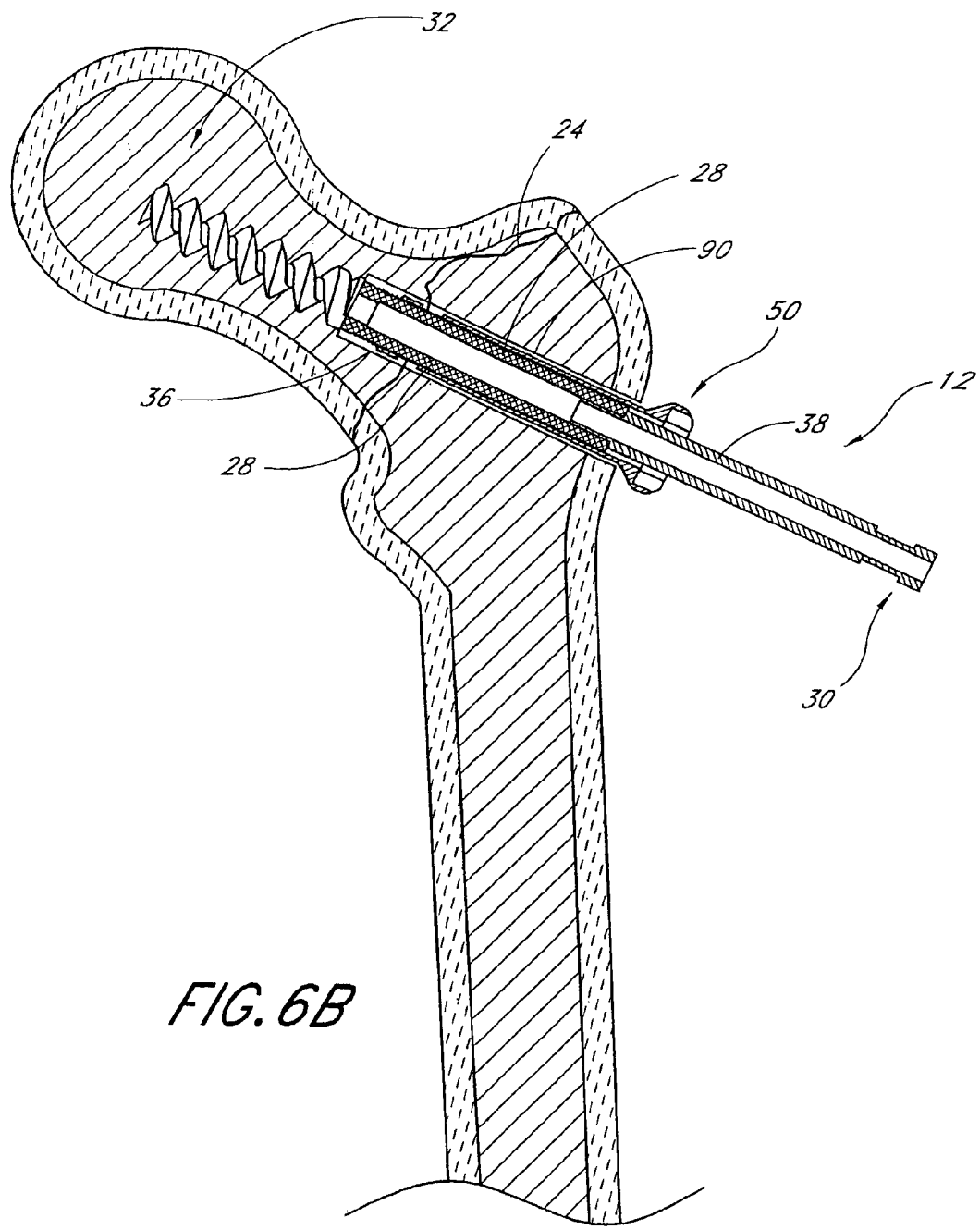
Figure 6C:
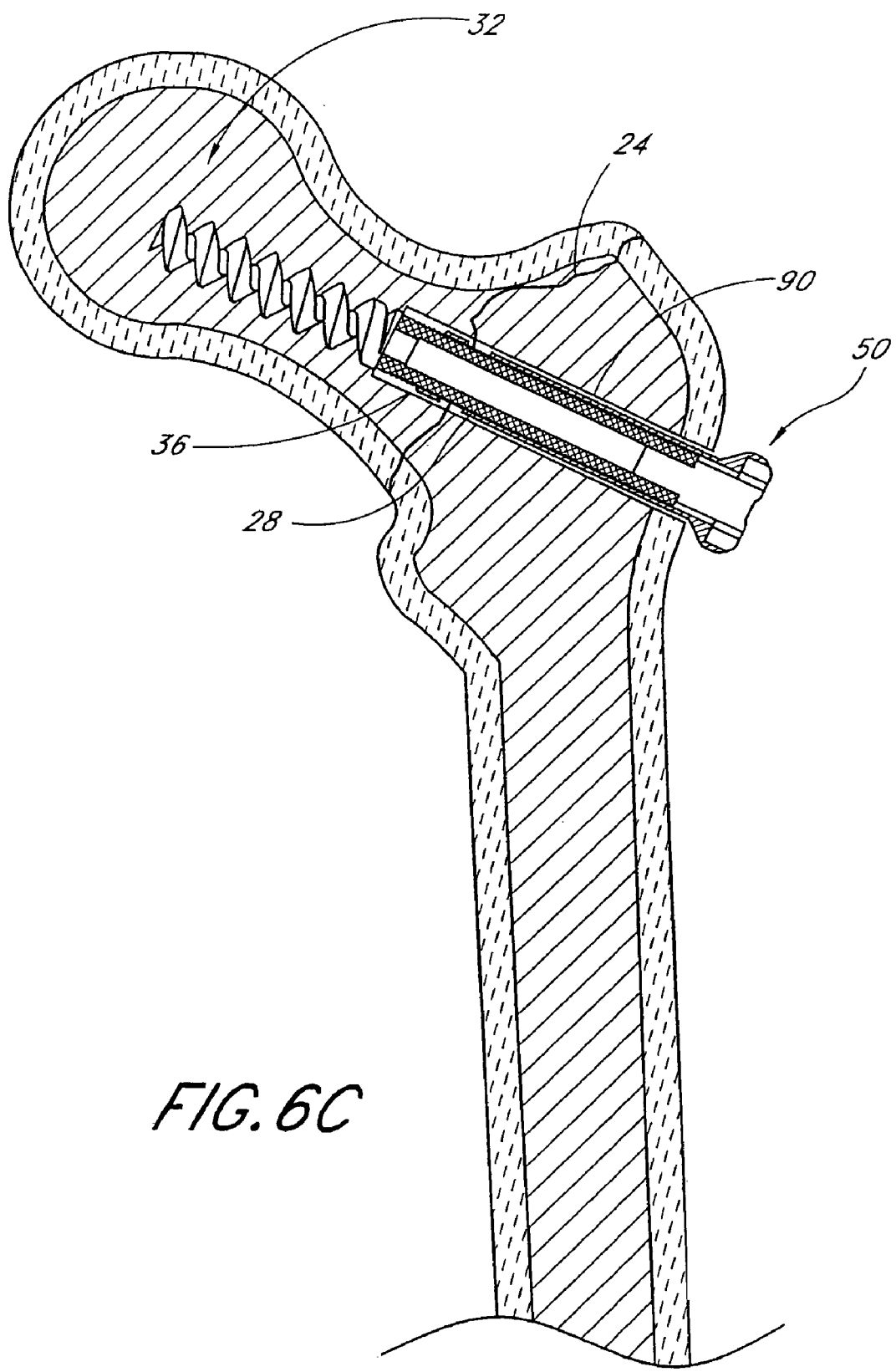

Once the distal tip of the anchor 34 is in the desired location, proximal traction is applied to the proximal end 30 of body 28, such as by the deployment devices described below or conventional hemostats, pliers or a calibrated loading device, while distal force is applied to the proximal anchor 50. In this manner, the proximal anchor 50 is advanced distally until the anchor 50 fits snugly against the outer surface of the femur or tissue adjacent the femur and the fracture 24 is completely reduced as shown in FIG. 6B. Appropriate tensioning of the fixation device 12 is accomplished by tactile feedback or through the use of a calibration device for applying a predetermined load on the implantation device. One advantage of the structure of the present invention is the ability to adjust compression independently of the setting of the distal anchor 34.

Following appropriate tensioning of the proximal anchor 50, the second portion 38 of the body 28 is preferably detached from the first portion 36 and removed. See FIG. 6C. In the illustrated embodiment, this involves rotating the second portion 38 with respect to the first portion via the coupling 70. In connection with many of the fractures identified previously herein, a single fixation device 12 may be all that is clinically indicated. However, two or three or more fixation devices 12 may be utilized to reduce a single fracture, depending upon the location and physical requirements of the fractured portion of the bone. For example, in the case of proximal femoral fractures of the type illustrated herein, typically at least two and preferably three fixation devices 12 will be implanted to span the femoral neck. The use of three fixation devices 12 desirably provides sufficient compression across the fracture, as well as minimizes the risk of rotation of the head of the femur around the axis of a single fixation device 12. The proximal end of the fixation devices may be connected together such as through a three-holed plate or rod, or may be independent of each other.

Following removal of the second portion 38 of each body 28, the access site may be closed and dressed in accordance with conventional wound closure techniques.

In a modified arrangement, the second portion 38 may form part of the driving device, which is used to rotate the proximal anchor 50 and thus cancellous bone anchor 34 into the head of the femur. The second portion 38 is used to apply proximal traction so as to compress the fracture. After appropriate tensioning, the second portion 38 can be decoupled from the first portion 36 and removed with the driving device.

In the foregoing variation, the second portion 38 may be connected to a rotatable control such as a thumb wheel on the deployment device. A container may be opened at the clinical site exposing the proximal end of the implant, such that the distal end of the second portion 38 may be removably coupled thereto. Proximal retraction of the hand tool will pull the implant out of its packaging. The implant may then be positioned within the aperture in the bone, rotated to set the distal anchor, and the hand piece may be manipulated to place proximal traction on the second portion 38 while simultaneously distally advancing the proximal anchor. Following appropriate tensioning across the fracture, the second portion 38 may be disengaged from the implant, and removed from the patient. In the example of a threaded engagement, the second portion 38 may be disengaged from the implant by rotating a thumb wheel or other rotational control on the hand piece. In an alternate embodiment, such as where the second portion 38 comprises a pull wire, following appropriate tensioning across the fracture, a first end of the pull wire is released such that the pull wire may be removed from the implant by proximal retraction of the second end which may be attached to the hand piece.

Preferably, the clinician will have access to an array of fixation devices 12, having, for example, different diameters, axial lengths and, if applicable, angular relationships. These may be packaged one per package in sterile envelopes or peelable pouches, or in dispensing cartridges which may each hold a plurality of devices 12. Upon encountering a fracture for which the use of a fixation device is deemed appropriate, the clinician will assess the dimensions and load requirements, and select a fixation device from the array, which meets the desired specifications.

In some instances, a clinician may want to introduce two or more fixation devices 12 into the femoral head 14 to secure the fracture 24. This may be desirable if the clinician determines that, based upon the nature of the fracture 24, there is a possibility that the head 14 of the femur 10 could rotate about a single fixation device 12. Even minor rotation can inhibit the healing of the fracture. Significant rotation can result in failure of the fixation device or necrosis of the femoral head. Two or more fixation devices 12 may also be desirable where the direction of the fracture is generally parallel to the axis of implantation as is understood in the art.

The fixation device 12 of the present invention may also be used in combination with intramedullary nails or rods, as will be understood by those of skill in the art.

The fixation device 12 of the present invention may be used in any of a wide variety of anatomical settings beside the proximal femur, as has been discussed. For example, lateral and medial malleolar fractures can be readily fixed using the device of the present invention. Referring to FIG. 7, there is illustrated an anterior view of the distal fibula 120 and tibia 122. The fibula 120 terminates distally in the lateral malleolus 124, and the tibia 122 terminates distally in the medial malleolus 126.

A fixation device 12 in accordance with the present invention is illustrated in FIG. 7 as extending through the lateral malleolus 124 across the lateral malleolar fracture 128 and into the fibula 120. Fixation device 12 includes a distal anchor 34 for fixation within the fibula 120, an elongate body 28 and a proximal anchor 50 as has been discussed.

FIG. 7 also illustrates a fixation device 12 extending through the medial malleolus 126, across a medial malleolar fracture 130, and into the tibia 122. Although FIG. 7 illustrates fixation of both a lateral malleolar fracture 128 and medial malleolar fracture 130, either fracture can occur without the other as is well understood in the art. Installation of the fixation devices across malleolar fractures is accomplished utilizing the same basic steps discussed above in connection with the fixation of femoral neck fractures.

The fixation devices of the present invention may be made from either conventional bioabsorbable materials or conventional non-absorbable materials, combinations thereof and equivalents thereof. In addition, natural materials such as allografts may be used. Examples of absorbable materials include homopolymers and copolymers of lactide, glycolide, trimethylene carbonate, caprolactone, and p-dioxanone and blends thereof. The following two blends may be useful: 1) the blend of poly(p-dioxanone) and a lactide/glycolide copolymer, as disclosed in U.S. Pat. No. 4,646,741 which is incorporated by reference and (2) the glycolide-rich blend of two or more polymers, one polymer being a high lactide content polymer, and the other being a high glycolide content disclosed in U.S. Pat. No. 4,889,119 which is incorporated by reference. Additional bioabsorbable materials are disclosed in copending application Ser. No. 09/558,057 filed Apr. 26, 2000, the disclosure of which is incorporated in its entirety herein by reference.

The fixation devices may also be made from conventional non-absorbable, biocompatible materials including stainless steel, titanium, alloys thereof, polymers, composites and the like and equivalents thereof. In one embodiment, the distal anchor comprises a metal helix, while the body and the proximal anchor comprise a bioabsorbable material. Alternatively, the distal anchor comprises a bioabsorbable material, and the body and proximal anchor comprise either a bioabsorbable material or a non-absorbable material. As a further alternative, each of the distal anchor and the body comprise a non-absorbable material, connected by an absorbable link. This may be accomplished by providing a concentric fit between the distal anchor and the body, with a transverse absorbable pin extending therethrough. This embodiment will enable removal of the body following dissipation of the pin, while leaving the distal anchor within the bone.

The components of the invention (or a bioabsorbable polymeric coating layer on part or all of the anchor surface), may contain one or more bioactive substances, such as antibiotics, chemotherapeutic substances, angiogenic growth factors, substances for accelerating the healing of the wound, growth hormones, antithrombogenic agents, bone growth accelerators or agents, and the like. Such bioactive implants may be desirable because they contribute to the healing of the injury in addition to providing mechanical support.

In addition, the components may be provided with any of a variety of structural modifications to accomplish various objectives, such as osteoincorporation, or more rapid or uniform absorption into the body. For example, osteoincorporation may be enhanced by providing a micropitted or otherwise textured surface on the components. Alternatively, capillary pathways may be provided throughout the body and collar, such as by manufacturing the anchor and body from an open cell foam material, which produces tortuous pathways through the device. This construction increases the surface area of the device which is exposed to body fluids, thereby generally increasing the absorption rate. Capillary pathways may alternatively be provided by laser drilling or other technique, which will be understood by those of skill in the art in view of the disclosure herein. In general, the extent to which the anchor can be permeated by capillary pathways or open cell foam passageways may be determined by balancing the desired structural integrity of the device with the desired reabsorption time, taking into account the particular strength and absorption characteristics of the desired polymer.

One open cell bioabsorbable material is described in U.S. Pat. No. 6,005,161 as a poly(hydroxy) acid in the form of an interconnecting, open-cell meshwork which duplicates the architecture of human cancellous bone from the iliac crest and possesses physical property (strength) values in excess of those demonstrated by human (mammalian) iliac crest cancellous bone. The gross structure is said to maintain physical property values at least equal to those of human, iliac crest, cancellous bone for a minimum of 90 days following implantation. The disclosure of U.S. Pat. No. 6,005,161 is incorporated by reference in its entirety herein.

FIGS. 8A-19 illustrate some exemplary embodiments of deployment devices usable with a bone fixation device such as those described above and in U.S. patent application Ser. No. 09/991,367, filed Nov. 13, 2001, entitled "METHOD AND APPARATUS FOR BONE FIXATION WITH SECONDARY COMPRESSION", application Ser. No. 09/991,367, which is hereby incorporated by reference herein. However, those skilled in the art will recognize that certain features and aspects of the deployment devices described below may also be used with a variety of other bone fixation devices. For example, the deployment devices may also be used with the bone anchors described in U.S. Pat. No. 6,632,224, issued Oct. 14, 2003, entitled "BONE FIXATION SYSTEM", which is hereby incorporated by reference in its entirety herein. The deployment device embodiments shown below are generally adapted to provide proximal traction, and/or axial rotation to a bone anchor. Those skilled in the art will recognize that many of the following deployment device embodiments, or portions thereof, may be modified and/or combined with one another to form further embodiments, and that no single feature is essential to the operation of the device. The various deployment device embodiments may be sized such that they are usable with a range of bone fixation devices, or they may be specifically sized and arranged for use with a particular model of bone fixation device.

Figure 8A:
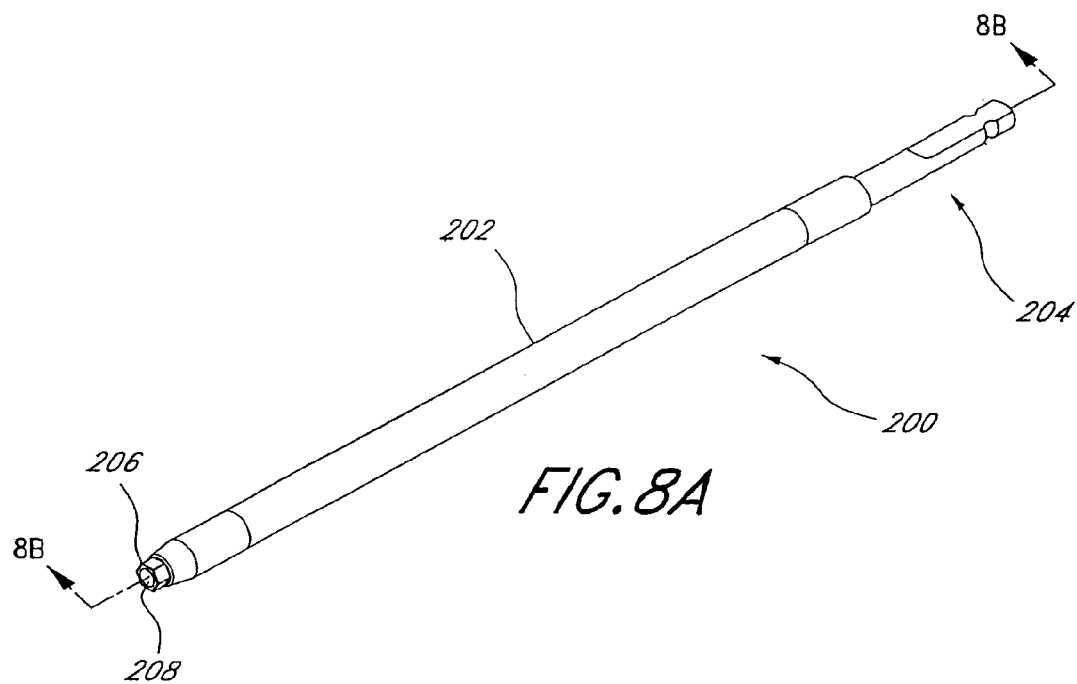
FIG. 8A is a perspective view of an embodiment of a deployment device for use with a bone fixation device.
Figure 8B:
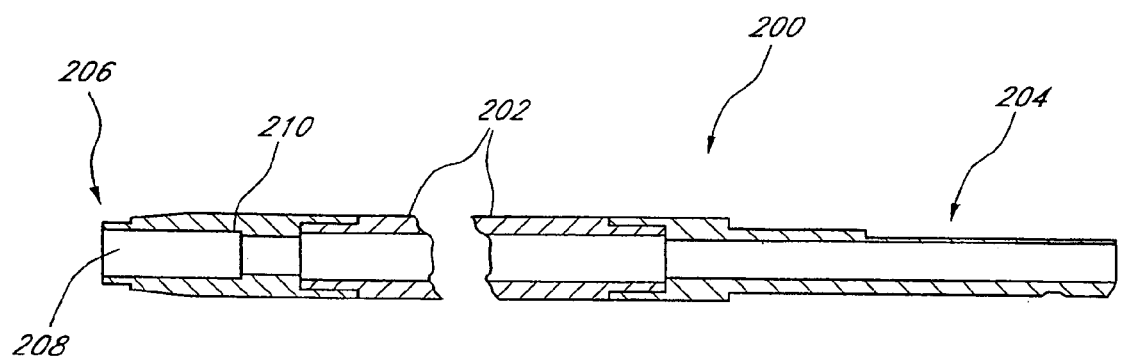
FIG. 8B is a section view taken through line 8B-8B of the bone fixation device of FIG. 8A.

One embodiment, as illustrated in FIGS. 8A and 8B is adapted to provide axial rotation to a bone anchor. The deployment device 200 of this embodiment includes an elongate body 202 with a handle-receiving portion 204 at a proximal end, and a distal end 206 adapted to engage a proximal end of a proximal bone anchor.

The distal end 206 of the deployment device 200 may include an axial hole 208 with a stop 210 at a depth sufficient to receive the distal end 32 of the body 28 of the bone anchor. In the illustrated embodiment, the outer portion of the distal end 206 is configured to engage the gripping structure of the proximal anchor 50. In the illustrated embodiment, the distal end is therefore hexagonal in shape and configured to be received by the hexagonal recess 84 of the proximal anchor 50. However, the distal end 206 can have any of a variety of different shapes for differently shaped gripping structures on the proximal anchor 50. For example, the distal end 206 can have a pentagonal shape or any other polygonal shape that is similar to the shape of the gripping structure (e.g., the recess 84) of the proximal anchor. In still other embodiments, the distal end may comprise a recess configured to engage a anti-rotational protrusion formed on the proximal anchor 50. In addition, the hole 208 preferably extends through the device 200 such that the device 200 may be used over a guidewire.

Figure 9:
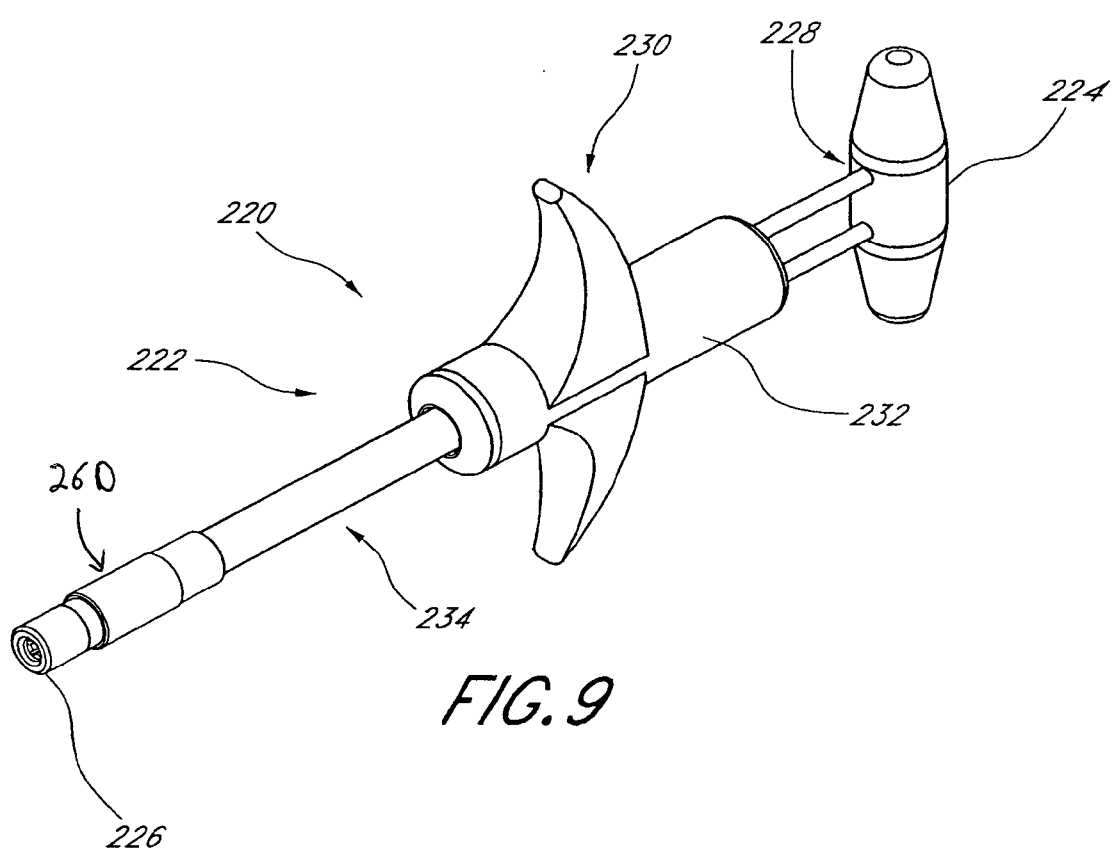
FIG. 9 is a perspective view of another embodiment of a bone fixation deployment device.
Figure 10:
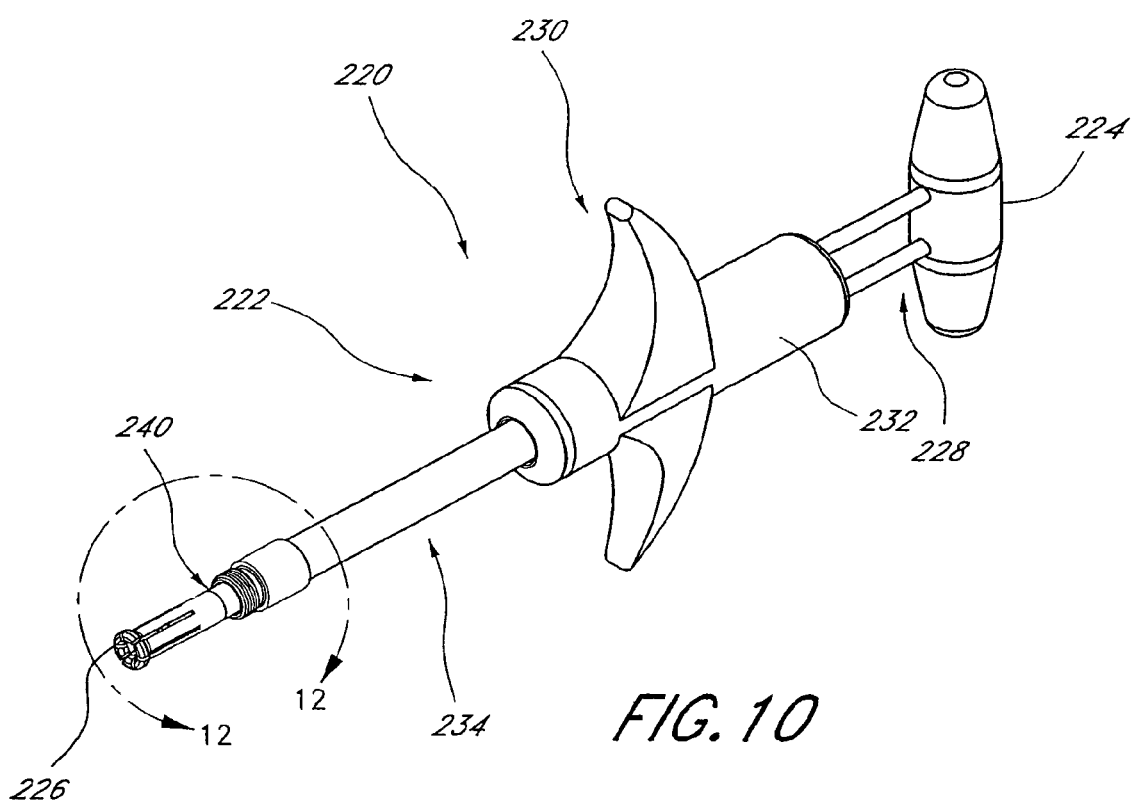
FIG. 10 is a perspective view of the deployment device of FIG. 9 with a distal cap removed.
Figure 11:
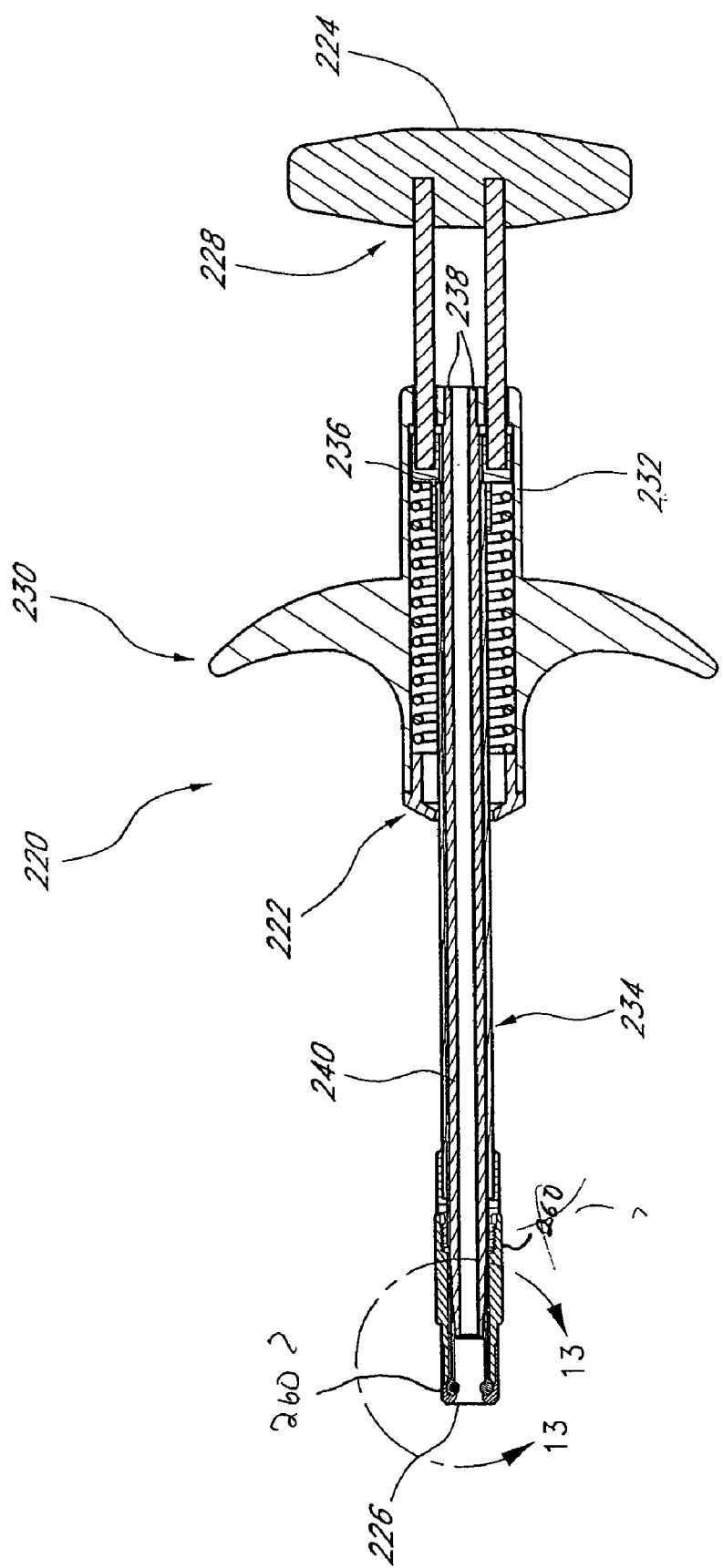
FIG. 11 is a section view of the deployment device of FIG. 9.

FIGS. 9-11 illustrate another embodiment of a deployment device 220. As will be explained below, this embodiment is generally configured to proximally retract the body 28 with respect to the proximal anchor 50. In certain embodiments, the deployment device 220 may be used in combination with the deployment device 200 of FIGS. 8A and 8B. In such embodiments, the deployment device 200 of FIG. 8A may be used to rotate the body 28 and the deployment device 220 of FIGS. 9-11 may be used to proximally retract the body 28 with respect to the proximal anchor 50. In other embodiments (see e.g., FIGS. 13 and 14), the device 220 is configured to also rotate the distal anchor 34. With initial reference to FIG. 9, in the illustrated embodiment, the device generally includes an elongate syringe-shaped body 222 having a proximal end 224, and a distal end 226. The deployment device 220 also generally comprises a first actuator, such as a palm engagement portion, such as a plunger 228, at the proximal end 224, a second actuator, such as a finger engagement portion, such as a finger grip 230 attached to a second component or inner component such as a proximal housing 232 located distally therefrom, and a first component or inner component such as an elongate distal housing 234 extending distally from the finger grip 230. As will be apparent from the description below, the device 220 preferably defines a lumen that extends through the device 220 such that it may be used over a guidewire.

With reference to FIG. 11, the illustrated embodiment also includes a tensioner member 240 that may be disposed within the distal housing 234. A distal end of the tensioner member 240 is positioned within a distal cap 260. As shown in FIG. 11 and explained below, the distal cap 260 may be removeably attached to the distal housing 234 by threads.

As will be explained below, the tensioner member 240 is configured to move with the finger grip 230. The member 240 and grip 230, in turn, move together relative to the plunger 224 and distal housing 234. The tensioner member 240, in turn, is preferably configured to grip a proximal end of the body 28 of the bone fixation device 12. In a modified embodiment, the distal housing 234 and the plunger 224 may be adapted to move together relative to the finger grip 230 and tensioner 240.

The provision of a tensioner member 240 on the deployment device 220 will generally allow a clinician to provide proximal traction to the body 28 of the bone fixation device 12. In the illustrated embodiment, the syringe-shaped body 222 is generally adapted such that application of a compressive force between the plunger 224 and the finger grip 230 results in engagement of the device 220 on a proximal end of the pin 28 (e.g., the rotational coupling 70 of FIG. 2) in order to provide proximal traction.

As mentioned above, the plunger 224 is generally adapted to be engaged by the heel of a clinician's hand, thus providing a comfortable handle by which the deployment device may be gripped for axial rotation, or a comfortable surface for the compressive force involved in providing traction to a bone fixation device as described elsewhere herein. Those skilled in the art will recognize that numerous specific arrangements of a plunger (or heel-engagement portion) may be provided according to the particular needs of the clinician. Similarly, the finger grip portion shown and described herein is merely provided by way of example. Those skilled in the art will recognize that other shapes and arrangements are available for providing a finger grip portion.

With reference to FIGS. 9-13, the plunger 228, finger grip 230, distal housing 234, and traction member 240 preferably cooperate to cause proximal motion of the traction member 240 relative to the housing 234 in response to a proximal motion of the finger grip 230 relative to the plunger 224. Those skilled in the art will recognize that many arrangements are possible to provide these desired motions, only some of which are described herein. In the illustrated emobodiment, the plunger 224 is attached to the distal housing 234 at a proximal portion 236 of the housing 234. The finger grip 230 is attached to a traction member 240 because the proximal end 238 of the traction member 240 is coupled to the proximal housing 232, which is connected to the grip 230. Thus, the finger grip 230 and traction member 240 can move together and the plunger 224 and distal housing 234 can move together. The traction member 240 can slidably engage the distal housing 234 as the grip 230 and plunger 224 are drawn towards each other.

Figure 20:
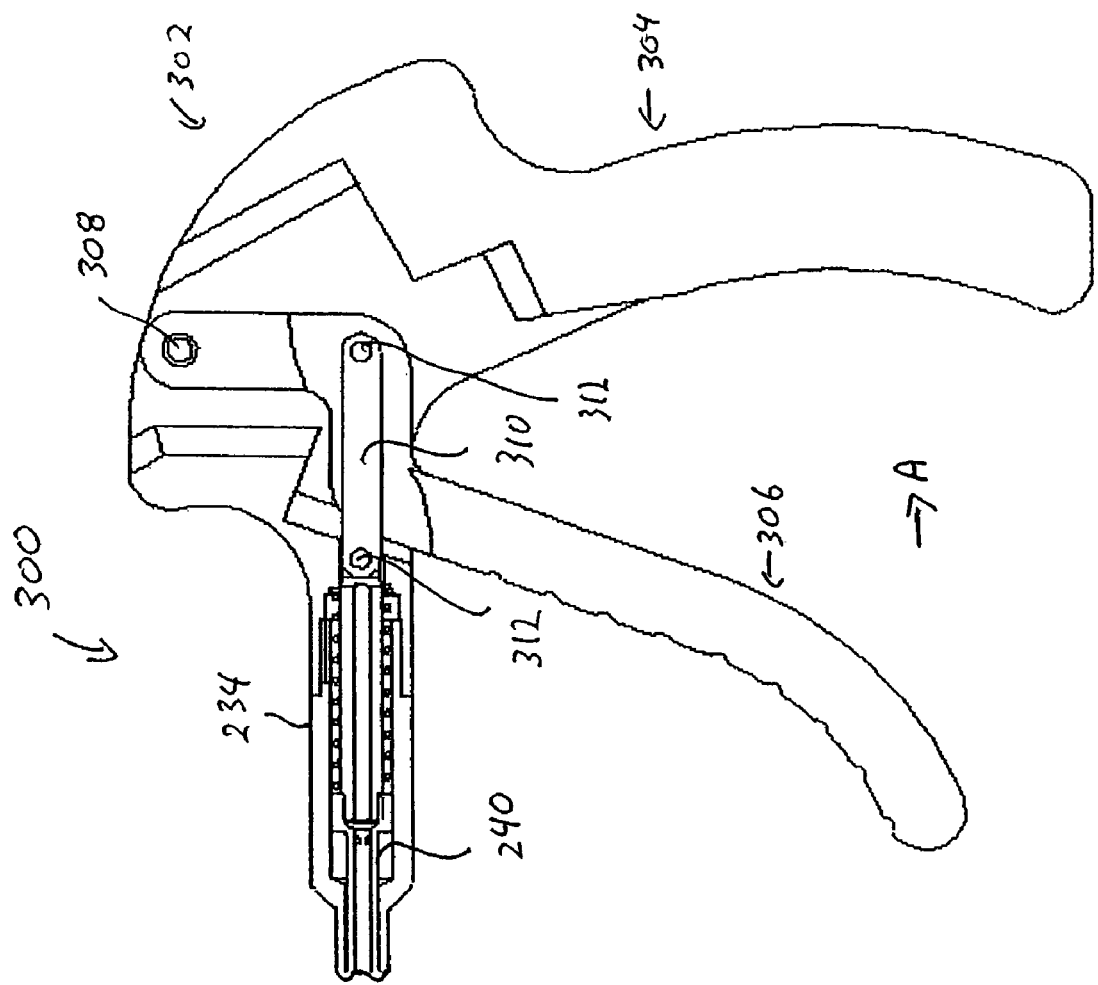
FIG. 20 is a cross-sectional side elevation view of an alternative embodiment of a proximal portion of a deployment device.

In the illustrated embodiment, the plunger 224 can be held generally stationary and the finger grip 230 can be can be pulled towards the plunger 224. The finger grip 230 and the traction member 240 can both move proximally relative the plunger 224 and the distal housing 234 as the traction member 240 slides smoothly along the distal housing 234. Of course, many other arrangements are possible for providing the desired motion of the traction member 240 relative to the distal housing 234 as a result of a compressive force. For example, as will be described below, FIG. 20 illustrates an embodiment which utilizes a pistol grip. In addition or in combination, the device may employ cable and pulley arrangements, levers, or other structures known to those skilled in the art. The various portions may be attached to one another by adhesives, welds, threads, mechanical fasteners, or any other suitable attachment method.

The traction member 240 may comprise a solid rod, a hollow tube, one or more cables, or any other appropriate structure such that it functions as described. The traction member 240 may be made of any suitable material known to those skilled in the art such that it has sufficient tensile strength that it will not stretch or otherwise deflect significantly during traction of the anchor. Suitable materials usable for the construction of a traction member include stainless steel, nylon, etc. and further materials (e.g., metals, plastic and the like) will be apparent to those skilled in the art.

Figure 12:
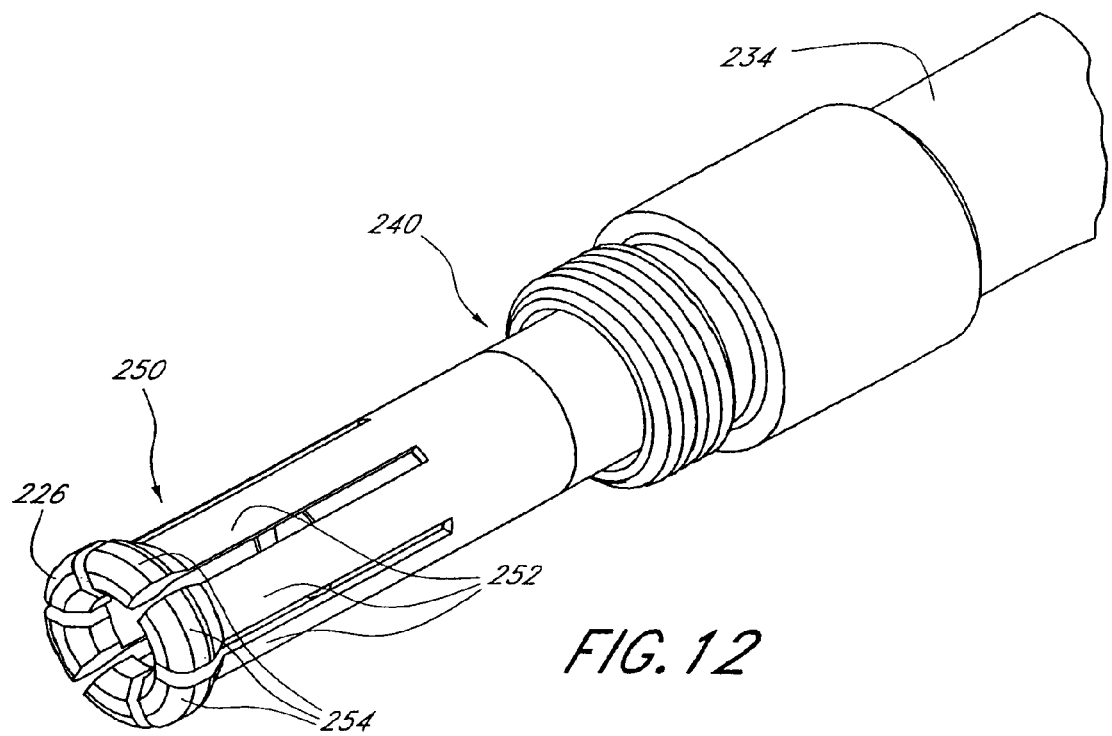
FIG. 12 is a detail view of a distal portion of the deployment device of FIG. 10.
Figure 13:
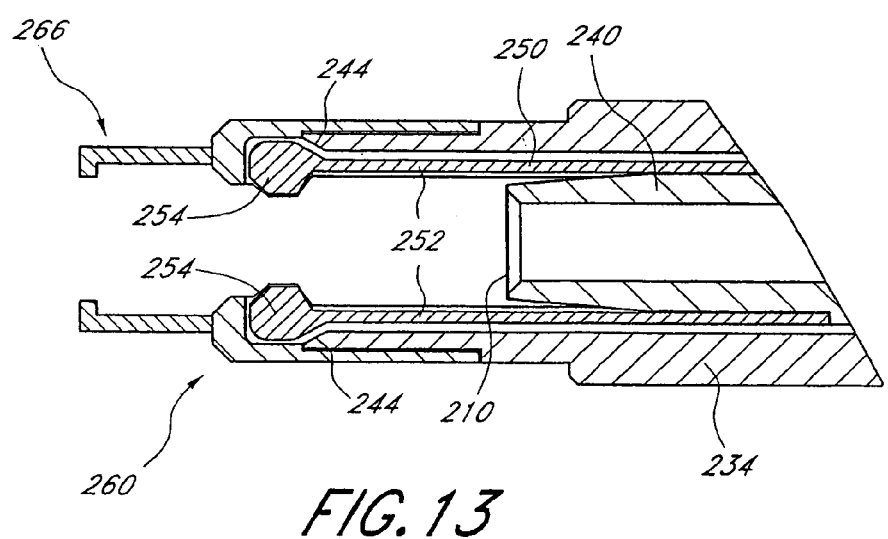
FIG. 13 is a detailed section view of the distal portion of the deployment device of FIG. 11.
Figure 14:
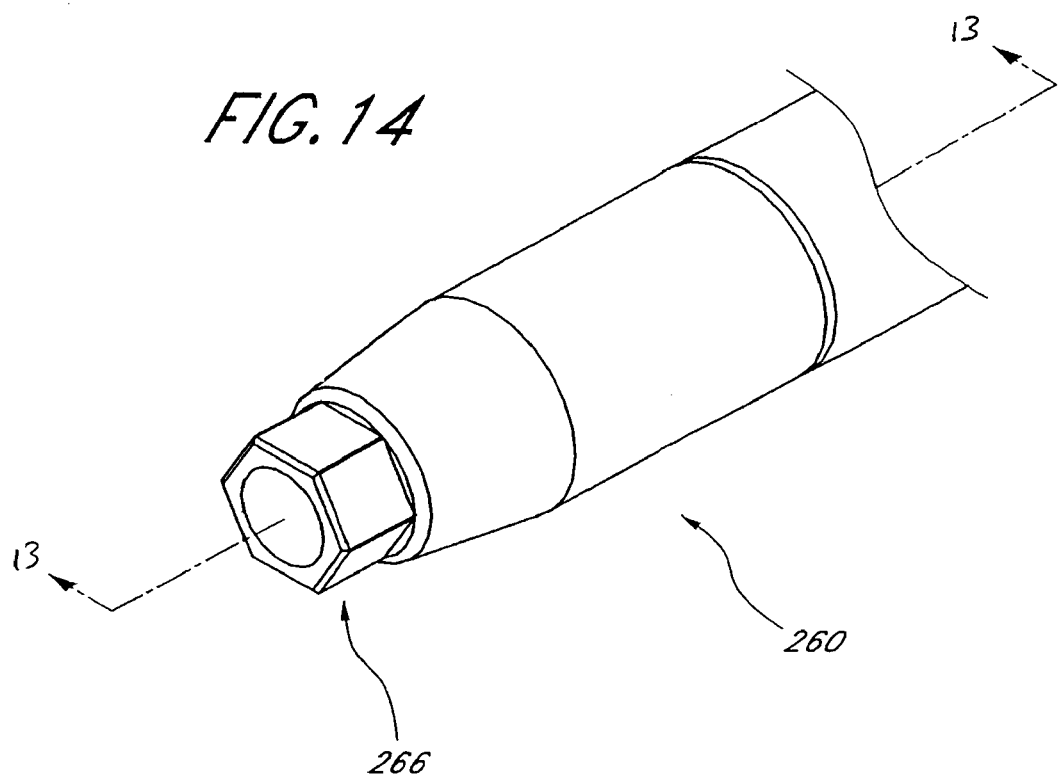
FIG. 14 is a detail view of a distal cap on a distal portion of a bone fixation device.

As seen best in FIGS. 12 and 13, the distal end of the traction member 240 comprises a collet 250 which is adapted to be closed around the proximal end 30 (see FIG. 2) of a bone fixation device 12. The collet 250 may be fixed to the distal end of the traction member 240 by any appropriate methods or devices, or the collet 250 and traction member 240 may be integrally formed. In one embodiment, the collet 250 is threaded onto the distal portion of the traction member 240. Providing a collet with threads advantageously allows collets of varying size may be used interchangeably with a single deployment device 220 in addition to increasing the ease of cleaning.

In the illustrated embodiment, the collet 250 comprises a plurality of flexible fingers 252, each having a gripping head 254 on its distal end. The flexible fingers 252 preferably have sufficient tensile strength that the collet 250 will provide sufficient proximal traction force to a bone fixation device when the deployment device is operated as described herein. In one embodiment, the gripping heads 254 comprise a polygonal cross section wherein the gripping head 254 joins to the finger 252 at one of the sides of the polygon. For example, the gripping head 254 may comprise an octagonal, hexagonal, quadrilateral, or other cross-sectional shape such that it functions as described herein. The functioning of the collet 250 will be described in further detail below with reference to FIGS. 17-19.

FIG. 13 is a detailed section view the collet 250 and with the removable distal cap 260 shown mounted to the distal end of the housing surrounding the collet 250 and traction member 240. In the embodiment shown, the distal edge of the distal housing 234 comprises a closing surface 244 formed by a constriction or reduction in diameter. The closing surface 244 causes the collet 250 to close as it moves distally relative to the collet 250. In one embodiment, the closing surfaces 244 can contact and move inwardly the gripping heads 254 as the closing surfaces 244 move distally relative the collet 250. The collet closing surface 244 may alternatively be provided as a constriction in the inner diameter of the distal cap 260.

As mentioned above, the distal cap 260 may be threaded or otherwise attached, such as by adhesives, welds, etc. to the distal housing 234. A removable distal cap, however, is preferred because it advantageously allows for greatly simplified cleaning of the deployment device tip. Many embodiments of a distal cap 260 may be provided depending on the particular application. A distal cap 260 such as that shown in FIG. 9, may be provided to abut the flange 66 of the proximal anchor 50 (see FIG. 18) for proximally retracting the anchor as discussed above. Alternatively, the distal cap 260 shown in FIGS. 13 and 14, comprises a hexagonal head 266 adapted to engage the hexagonal recess 84 of the proximal anchor 34 (see FIG. 4), and thus provide rotation of the fixation device 12, as described above. Of course in modified embodiments, the distal cap may include a different shape head or recess as appropriate given the structure of the proximal anchor 34.

Figure 15:
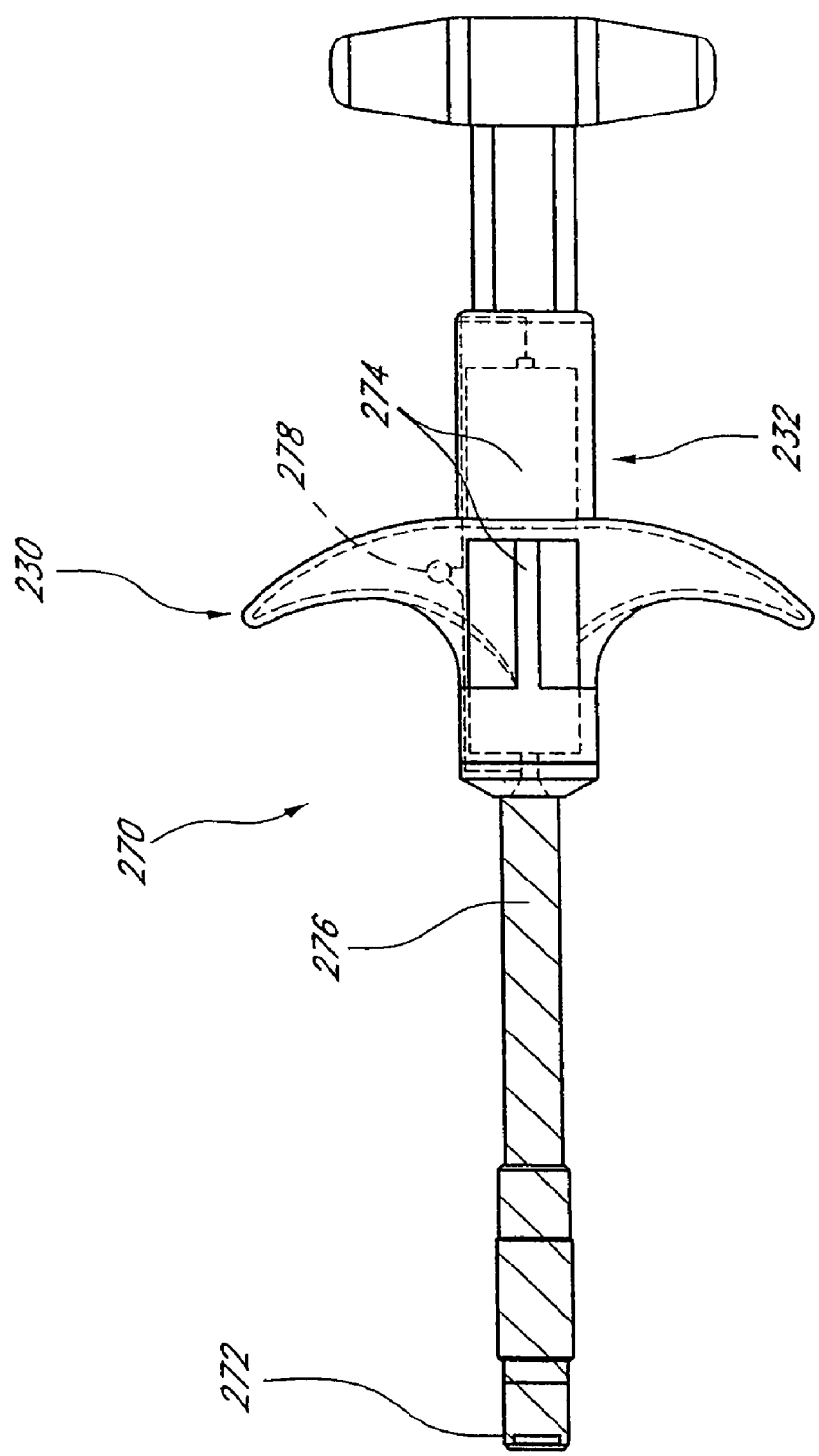
FIG. 15 is a side elevation of an alternative embodiment of a cauterizing deployment device.

FIG. 15 illustrates an embodiment of a cauterizing device 270 for a bone fixation deployment device. The device may be similar to any of the previous embodiments, and may include a cauterizing tip 272 for cutting an excess portion of a bioabsorbable, or other polymeric compression anchor after compression has been applied. The cauterizing tip 272 is typically used in conjunction with a one-piece body, as will be understood by those skilled in the art. According to this embodiment, the proximal housing 232 may be configured to provide space for a power supply 274 such as a battery. Alternatively, the cauterizing device 270 may be adapted to receive power from an external source such as an external battery or standard AC line power. The cauterizing tip 272 will typically be in electrical communication with the power source 274 such as by wires 276. A power switch 278 may be provided on the finger grip 230 in order to allow the cauterizing device 270 to be operated. The cauterizing tip 272 can be an electrical resistance heater adapted to heat and cut an excess portion of a pull pin of a bone fixation device. The cauterizing tip 272 may be provided as a removable distal cap 260 usable with any of the previously described embodiments. Similarly, the cauterizing device 270 may be configured to receive any of the structures of the previously described embodiments.

The one embodiment of use of the deployment device 220 will now be described with reference to FIGS. 16-18. In FIG. 16, the proximal pin 38 of a bone fixation device 12 has been inserted into the distal opening of the deployment device 220 as far as the stop 210 will allow. From this position, the bone fixation device 12 may be axially rotated as described above in order to anchor the distal anchor within the distal bone portion. In this embodiment shown in FIG. 16, a first component or distal cap 260 of the deployment device 220 includes the anti-rotational head 266 to engage the recess 84 of the proximal anchor 50. Once the distal anchor 34 has been positioned, the finger grip 230 and plunger 224 of the deployment device 220 are compressed, and as seen in FIG. 17, the traction member 240 moves proximally relative to the first component or distal housing 234 until the gripping heads 254 engage the closing surface 244, thereby causing the gripping heads 254 to be displaced toward the pin 38. As the traction member 240 continues to be proximally retracted, as shown in FIG. 18, the gripping heads 254 of a second member or collet 250 eventually engage the proximal flange 39 of the pin 38 thereby allowing the pin 38 and the distal anchor 34 to be pulled proximally relative to the proximal anchor 50. In some embodiments, when proximally withdrawing the elongate body 28 and/or pin 38 of the bone fixation device 12 with respect to the proximal anchor 50, a distal end of the second component does not extend axially beyond the distal end of the first component. For example, when proximally withdrawing the pin 38 with respect to the proximal anchor 50, the distal end of the second component, the gripping head 254 or distal end of the collet 250, does not extend axially beyond the distal end of the first component, the distal end of the distal housing 234 or the distal cap 260. Once the fixation device 12 has been sufficiently retracted, and the bone portions are held sufficiently rigidly, the pin 38 may be removed either by appropriate rotation in the case of the two-piece body 28 described above, or by cauterization or other cutting method in the case of a one-piece body.

Figure 19:
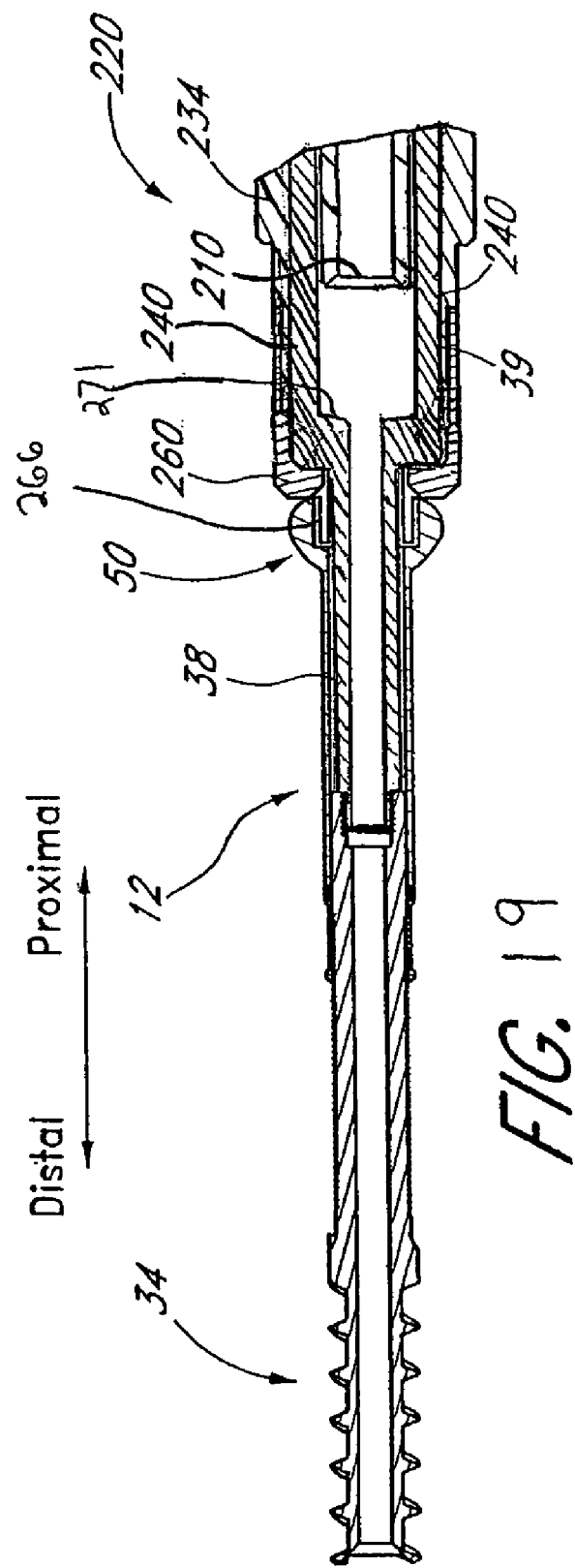
FIG. 19 is a section view illustrating another embodiment of a bone fixation device.

FIG. 19 is a section view of another embodiment of the deployment device 220. The proximal pin 38 of a bone fixation device 12 is attached to the distal end of the member 240 and passes through the distal opening of the deployment device 220. In one embodiment, the member 240 and the proximal pin 28 are a unitary body that is integrally formed. For example, the member 240 and proximal pin 28 can be formed of a single piece of material, such as metal. In another embodiment, the member 240 and proximal pin 28 are each integral bodies that are rigidly fixed to each other. For example, although not illustrated, the proximal end of the pin 38 can have a coupling structure, such as threads, adapted to engage a coupling structure of at the distal end of the member 240. Those skilled in the art recognize that there are many suitable manners of attaching the member 240 to the pin 38 for performing the functions described herein. In the illustrated embodiment, the distal cap 260 has distal end in the form of a head 266 which is adapted to engage a bone fixation device having a anti-rotational recess 84 for rotation of the flange 66 (see FIG. 4), and thus provide rotation of the fixation device 12, as described above.

The member 240 and the pin 38 can be coupled to the fixation device as illustrated in FIG. 19. From the illustrated position, the bone fixation device 12 may be axially rotated as described above in order to anchor the distal anchor within the distal bone portion. Once the distal anchor 34 has been positioned, the finger grip 230 and plunger 224 of the deployment device 220 are moved towards each other causing the member 240 and pin 38 to move proximally relative to the distal housing 234. The member 240 and pin 28 move together in the proximal direction until a seat 271 of the member 240 contacts the stop 210. Thus, pin 28 can be retracted into the distal end of the deployment device 200 by the simple relative movement of the plunger 224 and the finger grip 230. In one embodiment, the member 240 is rotatable such that second portion 38 of the body 28 may be removed by, for example, rotation of the second portion 38 with respect to the first portion 36. For example, in one embodiment, the member 240 extends through a proximal end of the plunger 224 and includes a twist knob such that the member 240 may be rotated to disengage the second portion 38 from the first portion 36 of the body 28. Those of skill in the art will recognize that the device 220 may be modified to accommodate other embodiments in which the first portion 36 and the second portion 38 of the body 28 are attached in other manners (e.g., releasable connectors such as eyes, hooks, transverse bars, etc.)

FIG. 20 is a cross-sectional view of another embodiment a deployment device 300 wherein like numbers are used to refer to like or similar components of previous embodiments. In the current embodiment, the distal end 226 of the device may be arranged as described above with reference to FIGS. 9-18. As such, only the proximal end 302 of the device is illustrated in FIG. 19. Instead of a plunger 228 and a finger grip 230, the proximal end 302 of the illustrated embodiment comprises a "pistol-grip" arrangement. Such an arrangement may include a stationary palm portion 304, which is coupled to the distal housing 234, and a trigger member 306, which is coupled to the tensioner 240. The trigger member 306 is pivotably connected to the stationary palm portion 304 by a pivot pin 308. The trigger member 306, in turn, may be coupled the tensioner 240 through a coupling member 310. The coupling member 310 may be pivotably connected to the trigger member 306 and the tensioner through pivot pins 312 and/or be formed from a flexible material. Accordingly, the tensioner 240 can be moved with respect to the housing 234 by squeezing the trigger member towards the palm portion 304 as indicated by arrow A.

The components of the present invention may be sterilized by any of the well known sterilization techniques, depending on the type of material. Suitable sterilization techniques include heat sterilization, radiation sterilization, such as cobalt 60 irradiation or electron beams, ethylene oxide sterilization, and the like.

The methods which are described and illustrated herein is not limited to the exact sequence of acts described, nor is it necessarily limited to the practice of all of the acts set forth. Other sequences of events or acts, or less than all of the events, or simultaneous occurrence of the events, may be utilized in practicing the embodiments of the invention. The specific dimensions of any of the bone fixation devices of the disclosed embodiments can be readily varied depending upon the intended application, as will be apparent to those of skill in the art in view of the disclosure herein. Moreover, although the present invention has been described in terms of certain preferred embodiments, other embodiments of the invention including variations in dimensions, configuration and materials will be apparent to those of skill in the art in view of the disclosure herein. In addition, all features discussed in connection with any one embodiment herein can be readily adapted for use in other embodiments herein. The use of different terms or reference numerals for similar features in different embodiments does not imply differences other than those which may be expressly set forth. Accordingly, the present invention is intended to be described solely by reference to the appended claims, and not limited to the preferred embodiments disclosed herein.

What is claimed is:

1. A deployment device for use with a bone fixation device, said deployment device comprising:
    a first component comprising a distal end and a proximal end, the distal end of the first component being configured to engage a proximal anchor of the bone fixation device;
    a palm engagement portion coupled to the first component;
    a second component comprising a distal end and a proximal end, the second component being axially moveable with respect to the first component;
    at least one finger engagement portion coupled to the second component and being positioned distally from the palm engagement portion, said finger engagement portion being movable relative to the palm engagement portion;
    a tensioner coupled to said second component and adapted to generally move with said finger engagement portion relative to said first component, said tensioner being configured to proximally withdraw an elongate body of the bone fixation device with respect to the proximal anchor which is carried by the elongate body as the at least one finger engagement portion is moved towards the palm engagement portion;
    wherein when proximally withdrawing the elongate body of the bone fixation device with respect to the proximal anchor, the distal end of the second component does not extend axially beyond the distal end of the first component.

2. The deployment device of claim 1, wherein the tensioner is configured to grip the elongate body of the fixation device as the at least one finger engagement portion is axially moved towards the palm engagement portion.

3. The deployment device of claim 1, wherein said distal end of said first component is configured to rotate the proximal anchor of the fixation device as the deployment device is rotated.

4. The deployment device of claim 3, wherein the distal end of the first component comprises a distal cap that is removeably attached to a remaining portion of the first component.

5. The deployment device of claim 1, wherein the deployment device is configured to separate the elongate body into a first portion and a second portion.

6. The deployment device of claim 5, wherein the deployment device comprises a cauterizing device.

7. The deployment device of claim 1, wherein said tensioner comprises a collet configured to grip the elongate body of the bone fixation device as the finger engagement portion moves proximally relative to the palm engagement portion.

8. The deployment device of claim 7, wherein the collet comprises a plurality of flexible fingers having gripping heads.

9. A deployment device for use with a bone fixation device comprising an elongate body with a distal helical anchor and a proximal anchor that is carried by the elongate body, said deployment device comprising:
    an outer component having a proximal end and a distal end;
    an inner component axially moveable within the outer component;
    a first actuator coupled to the outer component;
    a second actuator coupled to the inner component such that the first actuator is axially moveable with respect to the second actuator, the second actuator comprising a finger grip portion; and
    wherein the distal end of the outer component is configured to engage and rotate the proximal anchor of the bone fixation device and the inner component is removably coupled to the elongate body and configured such that proximal movement of inner component with respect to the outer component proximally withdraws the elongate body with respect to the proximal anchor.

10. The deployment device of claim 9, further comprising a distal cap being removeably attachable to the distal end of the outer component.

11. The deployment device of claim 10, wherein the distal cap comprises an anti-rotational head to engage a recess of the proximal anchor of the bone fixation device.

12. A deployment device for use with a bone fixation device comprising an elongate body with a distal helical anchor and a proximal anchor that is carried by the elongate body, said deployment device comprising:
    an outer component having a proximal end and a distal end;
    an inner component axially moveable within the outer component;
    a first actuator coupled to the outer component, the first actuator comprising a palm engagement portion;
    a second actuator coupled to the inner component such that the first actuator is axially moveable with respect to the second actuator; and
    wherein the distal end of the outer component is configured to engage and rotate the proximal anchor of the bone fixation device and the inner component is removably coupled to the elongate body and configured such that proximal movement of inner component with respect to the outer component proximally withdraws the elongate body with respect to the proximal anchor.

13. The deployment device of claim 12, further comprising a distal cap being removeably attachable to the distal end of the outer component.

14. The deployment device of claim 13, wherein the distal cap comprises an anti-rotational head to engage a recess of the proximal anchor of the bone fixation device.

15. A deployment device for use with a bone fixation device comprising an elongate body with a distal helical anchor and a proximal anchor that is carried by the elongate body, said deployment device comprising:
    an outer component having a proximal end and a distal end;
    an inner component axially moveable within the outer component;
    a first actuator coupled to the outer component;
    a second actuator coupled to the inner component such that the first actuator is axially moveable with respect to the second actuator; and wherein the distal end of the outer component is configured to engage and rotate the proximal anchor of the bone fixation device and the inner component is removably coupled to the elongate body by threads and configured such that proximal movement of inner component with respect to the outer component proximally withdraws the elongate body with respect to the proximal anchor.

16. The deployment device of claim 15, further comprising a distal cap being removeably attachable to the distal end of the outer component.

17. The deployment device of claim 16, wherein the distal cap comprises an anti-rotational head to engage a recess of the proximal anchor of the bone fixation device.

18. A deployment device for use with a bone fixation device comprising an elongate body with a distal helical anchor and a proximal anchor that is carried by the elongate body, said deployment device comprising:
   an outer component having a proximal end and a distal end;
   an inner component axially moveable within the outer component, the inner component being adapted to grip the elongate body of the fixation device;
   a first actuator coupled to the outer component;
   a second actuator coupled to the inner component such that the first actuator is axially moveable with respect to the second actuator; and
   wherein the distal end of the outer component is configured to engage and rotate the proximal anchor of the bone fixation device and the inner component is removably coupled to the elongate body and configured such that proximal movement of inner component with respect to the outer component proximally withdraws the elongate body with respect to the proximal anchor.

19. The deployment device of claim 18, wherein the inner component comprises a tensioner having a collet configured to grip the elongate body of the bone fixation device as the first actuator moves proximally relative to the second actuator.

20. The deployment device of claim 19, wherein the collet comprises a plurality of flexible fingers having gripping heads.

* * * * *